US009689932B2

(12) United States Patent
Bontus et al.

(10) Patent No.: US 9,689,932 B2
(45) Date of Patent: Jun. 27, 2017

(54) APPARATUS AND METHOD FOR INFLUENCING AND/OR DETECTING MAGNETIC PARTICLES HAVING A LARGE FIELD OF VIEW

(71) Applicant: KONINKLIJKE PHILIPS N.V., Eindhoven (NL)

(72) Inventors: Claas Bontus, Hamburg (DE); Ingo Schmale, Hamburg (DE); Bernhard Gleich, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 241 days.

(21) Appl. No.: 14/357,795

(22) PCT Filed: Nov. 13, 2012

(86) PCT No.: PCT/IB2012/056376
§ 371 (c)(1),
(2) Date: May 13, 2014

(87) PCT Pub. No.: WO2013/072841
PCT Pub. Date: May 23, 2013

(65) Prior Publication Data
US 2014/0306698 A1    Oct. 16, 2014

Related U.S. Application Data

(60) Provisional application No. 61/560,323, filed on Nov. 16, 2011, provisional application No. 61/560,327, (Continued)

(51) Int. Cl.
*G01V 3/00* (2006.01)
*A61B 5/05* (2006.01)
(Continued)

(52) U.S. Cl.
CPC ............ *G01R 33/02* (2013.01); *A61B 5/0515* (2013.01); *G01N 27/72* (2013.01)

(58) Field of Classification Search
CPC ............................. G01N 27/023; G01V 3/00
(Continued)

(56) References Cited

U.S. PATENT DOCUMENTS 6,487,436 B1    11/2002  Boskamp et al.
6,630,829 B1    10/2003  Liu
(Continued)

FOREIGN PATENT DOCUMENTS

DE          10151778        5/2003
EP          1304542         4/2014
(Continued)

OTHER PUBLICATIONS

B. Gleich et al., "Tomographic Imaging Using the Nonlinear Response of Magnetic Particles", Natures, vol. 435, Jun. 30, 2005, pp. 1214-1217.

*Primary Examiner* — Bot Ledynh

(57) ABSTRACT

The present invention relates to an apparatus and a method for influencing and/or detecting magnetic particles in a field of view (28), in particular for examination of human patients. The apparatus comprises i) selection-and-focus means (120) for generating a magnetic selection-and-focus field (50), wherein said at least one set of selection-and-focus field coils comprises—at least one inner selection-and-focus field coil (113, 115) being formed as a closed loop about an inner coil axis (115a), first inner selection-and-focus field coil (115)—a group of at least two outer selection-and-focus field coils (116-119) arranged at a larger distance from said inner coil axis (115a) than said at least one inner selection-and-focus field coil (113, 115) and at different angular positions, each being formed as a closed loop about an associated outer coil axis (116a-119a), and ii)
(Continued)

drive means (120) comprising a drive field signal generator unit (122) and drive field coils (124; 125, 126, 127) for changing the position in space and/or size of the two sub-zones (52, 54) in the field of view (28) by means of a magnetic drive field so that the magnetization of the magnetic material changes locally.

15 Claims, 25 Drawing Sheets

Related U.S. Application Data filed on Nov. 16, 2011, provisional application No. 61/662,413, filed on Jun. 21, 2012, provisional application No. 61/662,423, filed on Jun. 21, 2012.

(51) Int. Cl.
  *G01V 3/10* (2006.01)
  *G01R 33/02* (2006.01)
  *G01N 27/72* (2006.01)

(58) Field of Classification Search
  USPC .................................................. 324/234, 308
  See application file for complete search history.

(56) References Cited

U.S. PATENT DOCUMENTS

| | | | |
|---|---|---|---|
| 6,870,369 | B2 | 3/2005 | Yoshida |
| 6,982,554 | B2 | 1/2006 | Kurpad et al. |
| 7,336,074 | B2 | 2/2008 | Yang et al. |
| 8,971,988 | B2 * | 3/2015 | Borgert et al. ............ 600/409 |
| 2007/0052419 | A1 | 3/2007 | Overweg |
| 2008/0309330 | A1 | 12/2008 | Ohyu et al. |
| 2010/0045280 | A1 | 2/2010 | Gleich et al. |
| 2010/0164492 | A1 | 7/2010 | Leussler |
| 2012/0065491 | A1 * | 3/2012 | Borgert et al. ............ 600/409 |

FOREIGN PATENT DOCUMENTS

| | | |
|---|---|---|
| WO | WO2004091386 | 10/2004 |
| WO | WO2004091390 | 10/2004 |
| WO | WO2004091394 | 10/2004 |
| WO | WO2004091395 | 10/2004 |
| WO | WO2004091396 | 10/2004 |
| WO | WO2004091397 | 10/2004 |
| WO | WO2004091398 | 10/2004 |
| WO | WO2004091408 | 10/2004 |
| WO | WO2010134006 | 11/2010 |
| WO | WO2011095916 | 8/2011 |
| WO | WO2012077015 | 6/2012 |

* cited by examiner

ND METHOD FOR
INFLUENCING AND/OR DETECTING
MAGNETIC PARTICLES HAVING A LARGE
FIELD OF VIEW

CROSS-REFERENCE TO PRIOR APPLICATIONS

This application is the U.S. National Phase application under 35 U.S.C. §371 of International Application Serial No. PCT/IB2012/056376, filed on Nov. 13, 2012, which claims the benefit of U.S. applications Ser. Nos. 61/560,323, filed on Nov. 16, 2011; 61/560,327, filed on Nov. 16, 2011; 61/662,413, filed on Jun. 21, 2012 and 61/662,423, filed on Jun. 21, 2012. These applications are hereby incorporated by reference herein.

FIELD OF THE INVENTION

The present invention relates to an apparatus and a method for influencing and/or detecting magnetic particles in a field of view. Further, the present invention relates to a coil arrangement and/or a pole shoe. The present invention relates particularly to the field of Magnetic Particle Imaging.

BACKGROUND OF THE INVENTION

Magnetic Particle Imaging (MPI) is an emerging medical imaging modality. The first versions of MPI were two-dimensional in that they produced two-dimensional images. Newer versions are three-dimensional (3D). A four-dimensional image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MP image of an object's volume of interest is generated in two steps. The first step, referred to as data acquisition, is performed using an MPI scanner. The MPI scanner has means to generate a static magnetic gradient field, called the "selection field", which has a (single) field-free point (FFP) or a field-free line (FFL) at the isocenter of the scanner. Moreover, this FFP (or the FFL; mentioning "FFP" in the following shall generally be understood as meaning FFP or FFL) is surrounded by a first sub-zone with a low magnetic field strength, which is in turn surrounded by a second sub-zone with a higher magnetic field strength. In addition, the scanner has means to generate a time-dependent, spatially nearly homogeneous magnetic field. Actually, this field is obtained by superposing a rapidly changing field with a small amplitude, called the "drive field", and a slowly varying field with a large amplitude, called the "focus field". By adding the time-dependent drive and focus fields to the static selection field, the FFP may be moved along a predetermined FFP trajectory throughout a "volume of scanning" surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles or other magnetic non-linear materials; if the object is an animal or a patient, a contrast agent containing such particles is administered to the animal or patient prior to the scan.

During the data acquisition, the MPI scanner moves the FFP along a deliberately chosen trajectory that traces out/covers the volume of scanning, or at least the field of view. The magnetic nanoparticles within the object experience a changing magnetic field and respond by changing their magnetization. The changing magnetization of the nanoparticles induces a time-dependent voltage in each of the receive coils. This voltage is sampled in a receiver associated with the receive coil. The samples output by the receivers are recorded and constitute the acquired data. The parameters that control the details of the data acquisition make up the "scan protocol".

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model can be formulated as an integral operator that acts on the acquired data; the reconstruction algorithm tries to undo, to the extent possible, the action of the model.

Such an MPI apparatus and method have the advantage that they can be used to examine arbitrary examination objects—e.g. human bodies—in a non-destructive manner and with a high spatial resolution, both close to the surface and remote from the surface of the examination object. Such an apparatus and method are generally known and have been first described in DE 101 51 778 A1 and in Gleich, B. and Weizenecker, J. (2005), "Tomographic imaging using the nonlinear response of magnetic particles" in Nature, vol. 435, pp. 1214-1217, in which also the reconstruction principle is generally described. The apparatus and method for magnetic particle imaging (MPI) described in that publication take advantage of the non-linear magnetization curve of small magnetic particles.

The design of the MPI apparatus and methods described so far are not yet optimal for human beings.

SUMMARY OF THE INVENTION

It is an object of the present invention to provide an apparatus and a method for influencing and/or detecting magnetic particles in a field of view that enables the examination of larger subjects (human beings, animals), in particular for adult human beings.

In a first aspect of the present invention an apparatus for influencing and/or detecting magnetic particles in a field of view is presented comprising:

i) selection-and-focus means for generating a magnetic selection-and-focus field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view and for changing the position in space of the field of view within an examination area, said selection-and-focus means comprising at least one set of selection-and-focus field coils and a selection-and-focus field generator unit for generating selection-and-focus field currents to be provided to said at least one set of selection-and-focus field coils for controlling the generation of said magnetic selection-and-focus field,
wherein said at least one set of selection-and-focus field coils comprises
  at least one inner selection-and-focus field coil being formed as a closed loop about an inner coil axis, and
  a group of at least two outer selection-and-focus field coils arranged at a larger distance from said inner coil axis than said at least one inner selection-and-focus field coil and at different angular positions, each being formed as a closed loop about an associated outer coil axis, and
ii) drive means comprising a drive field signal generator unit and drive field coils for changing the position in space and/or size of the two sub-zones in the field of view by means of a magnetic drive field so that the magnetization of the magnetic material changes locally.

In a further aspect of the present invention a corresponding method is presented.

In a still further aspect of the present invention a coil arrangement is presented for use as selection-and-focus field coil arrangement in an apparatus for influencing and/or detecting magnetic particles in a field of view, said coil arrangement comprising at least one set of selection-and-focus field coils comprising:
  at least one inner selection-and-focus field coil being formed as a closed loop about an inner coil axis, and
  a group of at least two outer selection-and-focus field coils arranged at a larger distance from said inner coil axis than said at least one inner selection-and-focus field coil and at different angular positions, each being formed as a closed loop about an associated outer coil axis.

In an embodiment of the present invention at least one pole shoe, having a number of pole shoe segments carrying the various selection-and-focus field coils and a pole shoe yoke connecting said pole shoe segments, is provided in an apparatus for influencing and/or detecting magnetic particles in a field of view. It may be provided for carrying coils of a set of selection-and-focus field coils comprising at least one inner selection-and-focus field coil being formed as a closed loop about an inner coil axis, and a group of at least two outer selection-and-focus field coils arranged at a larger distance from said inner coil axis than said at least one inner selection-and-focus field coil and at different angular positions, each being formed as a closed loop about an associated outer coil axis,
said pole shoe comprising
  at least one inner pole shoe segment for carrying said at least one inner selection-and-focus field coil,
  at least two outer pole shoe segments arranged at a larger distance from said inner coil axis, each for carrying one of said at least two outer selection-and-focus field coils, and
  a pole shoe yoke connecting said pole shoe segments.

In an embodiment a computer program is presented comprising program code means for causing a computer to control an apparatus according to the present invention to carry out the steps of the method according to the present invention when said computer program is carried out on the computer.

Preferred embodiments of the invention are defined in the dependent claims. It shall be understood that the claimed method and the claimed coil arrangement, and pole shoe have similar and/or identical preferred embodiments as the claimed apparatus and as defined in the dependent claims.

The present invention is based on the idea to combine the focus field coils and the selection field coils that are generally provided as separate coils in the known MPI apparatus into a combined set of selection-and-focus field coils. Hence, a single current is provided to each of said coils rather than separate currents as conventionally provided to each focus field coil and each selection field coil. The single currents can thus be regarded as two superposed currents for focus field generation and selection field generation. The desired location and movement of the field of view within the examination area can be easily changed by controlling the currents to the various coils. Not all selection-and-focus field coils must, however, always be provided with control currents, but some coils are only needed for certain movements of the field of view.

The proposed apparatus of the coils further provides more freedom of how and where to arrange the coils with respect to the examination area in which the subject is placed. It is particularly possible with this arrangement to build an open scanner that is easily accessible both by the patient and by doctors or medical personnel, e.g. a surgeon during an intervention.

According to the present invention the magnetic gradient field (i.e. the magnetic selection field) is generated with a spatial distribution of the magnetic field strength such that the field of view comprises a first sub-area with lower magnetic field strength (e.g. the FFP), the lower magnetic field strength being adapted such that the magnetization of the magnetic particles located in the first sub-area is not saturated, and a second sub-area with a higher magnetic field strength, the higher magnetic field strength being adapted such that the magnetization of the magnetic particles located in the second sub-area is saturated. Due to the non-linearity of the magnetization characteristic curve of the magnetic particles the magnetization and thereby the magnetic field generated by the magnetic particles shows higher harmonics, which, for example, can be detected by a detection coil. The evaluated signals (the higher harmonics of the signals) contain information about the spatial distribution of the magnetic particles, which again can be used e.g. for medical imaging, for the visualization of the spatial distribution of the magnetic particles and/or for other applications.

Thus, the apparatus and the method according to the present invention are based on a new physical principle (i.e. the principle referred to as MPI) that is different from other known conventional medical imaging techniques, as for example nuclear magnetic resonance (NMR). In particular, this new MPI-principle, does, in contrast to NMR, not exploit the influence of the material on the magnetic resonance characteristics of protons, but rather directly detects the magnetization of the magnetic material by exploiting the non-linearity of the magnetization characteristic curve. In particular, the MPI-technique exploits the higher harmonics of the generated magnetic signals which result from the non-linearity of the magnetization characteristic curve in the area where the magnetization changes from the non-saturated to the saturated state.

According to a preferred embodiment said closed loops of the outer selection-and-focus field coils have a contour in the form of a ring segment. In other words, the windings of each of said outer selection-and-focus field coils are wound as a closed loop, which is arranged along an angular area around said at least one inner selection-and-focus field coil, which angular area covers a ring segment of a ring enclosing said at least one inner selection-and-focus field coil.

Preferably, said at least one set of selection-and-focus field coils comprises a group of at least four outer selectionand-focus field coils. Generally, even more selection-and-focus field coils may be provided which are preferably arranged at the same distance from the inner coil axis but at different angular positions around said inner coil axis.

For instance, in an embodiment it is provided that said at least one set of selection-and-focus field coils comprises a group of four outer selection-and-focus field coils being arranged at the same distance from the inner coil axis but angularly displaced by 90° with respect to each other. In further embodiments even more groups of outer selection-and-focus field coils, the coils of the various groups being arranged at different distances from the inner coil axis.

In another embodiment said at least one set of selection-and-focus field coils comprises a first inner selection-and-focus field coil and a second inner selection-and-focus field coil being formed as a closed loop about said inner coil axis and having a larger diameter than said first inner selection-and-focus field coil. Even more inner selection-and-focus field coil formed as closed loops about the inner coil axis at different distances may be provided. These inner selection-and-focus field coil are generally more effective for generation of the magnetic selection and focus fields and are, hence, generally provided with control currents all the time during operation of the apparatus.

Preferably, said at least one inner selection-and-focus field coil and/or said outer selection-and-focus field coils are split into at least two, in particular at least four, coil segments, wherein coil segments of a coil are arranged adjacent to each other in the direction of the associated coil axis and wherein adjacent coil segments are electrically connected. In this way the desired current density can be controlled to be higher at certain areas, in particular closer to the examination area, i.e. said coils segments are preferably arranged such that in the direction of the associated coils axis the obtained current density increases with decreasing distance from the examination area. This further increases the efficiency of the generated magnetic fields.

For the purpose of controlling the desired current density different measures with respect to the coil segments can be taken. In particular, one or more coil segments of a coil arranged closer to the examination area are, compared to one or more coil segments of the same coil arranged farther away from the examination area, made of a different material, have thicker windings, are more compact and/or have a higher thickness in the direction of the associated coil axis.

In a preferred embodiment said selection-and-focus means further comprises at least one pole shoe having a number of pole shoe segments carrying the various selection-and-focus field coils and a pole shoe yoke connecting said pole shoe segments. Such a pole shoe does not only serve as a mechanical carrier for the various coils, but also for increasing the efficiency of the magnetic fields by conducting the magnetic flux.

Preferably, said at least one pole shoe comprises a at least one inner pole shoe segment carrying said at least one inner selection-and-focus field coil and at least two outer pole shoe segments arranged at a larger distance from said inner coil axis and each carrying one of said at least two outer selection-and-focus field coils. Thus, the design of the pole shoe is adapted to the design of the selection-and-focus field coils to optimally support the efficiency of the magnetic field generation.

Preferably, said at least one pole shoe comprises at least four outer pole shoe segments each carrying an outer selection-and-focus field coil. Thus, for each outer selection-and-focus field coil an outer pole shoe segment is provided for guiding the magnetic field of the associated selection-and-focus coil. Thus, in an embodiment for the corresponding design of the outer selection-and-focus coils said at least one pole shoe comprises four outer pole shoe segments each carrying an outer selection-and-focus field coil, said outer pole shoe segments being arranged at the same distance from the inner coil axis but angularly displaced by 90° with respect to each other. Still further, each outer pole shoe segment preferably has a cross section in the form of a ring segment.

In still another embodiment, in which said selection-and-focus coil comprises a second inner selection-and-focus coil, said at least one pole shoe comprises a second inner pole shoe segment in the form of a closed ring around said first inner pole shoe segment, said second inner pole shoe segment carrying said second inner selection-and-focus field coil.

In a preferred embodiment at least the at least one inner pole shoe segment and head portions of the outer pole shoe segments facing the examination area are made from a soft-magnetic material having a high saturation induction, in particular FeCo, FeSi, Fe, FeNi, Dy, Gd or an alloy thereof such as $Fe_{49}V_{1.9}Co_{49}$. Preferably, the complete pole shoe should be made of the best soft-magnetic material that best guides the magnetic flux. However, for cost reasons only part of the pole is made from this material to have the best saturation magnetization there. The tail portions of the outer pole shoe segments facing away from the examination area and the pole shoe yoke are made from a soft-magnetic material having a lower saturation induction than the material of the inner pole shoe segments, in particular FeSi, FeNi, Permalloy or an alloy thereof such as $Fe_{73.5}Cu_1Nb_3Si_{15.5}B_7$.

Further, in an embodiment the pole shoes are made from magnetically conductive sheets, wherein sheets forming the pole shoe segments and an adjacent head portion of the pole shoe yoke are arranged in a direction parallel to the inner coil axis. The sheets are used to suppress eddy currents and are arranged to be conduct the magnetic flux.

Preferably, sheets forming the tail portion of the pole shoe yoke are arranged in a direction perpendicular to the inner coil axis. This allows guidance of the magnetic flux while eddy currents are suppressed.

In an embodiment said selection-and-focus means further comprises a pole shoe bearing connecting said pole shoes mechanically, said pole shoe bearing being made of a magnetically conductive material. Said pole shoe bearing is preferably also made from magnetically conductive sheets that are arranged adjacent to each other in the same direction as sheets forming the portion of the pole shoe to which the pole shoe bearing is connected. The pole shoe bearing should both provide a mechanical stability and a good magnetic flux.

In an advantageous embodiment said at least one inner pole shoe segment and said at least one inner selection-and-focus field coil are arranged at a larger distance from the examination area than said outer pole shoe segments and said outer selection-and-focus field coils. This provides the advantage that there is more space for arranging the drive field coils, particularly in case of an apparatus comprising two opposingly arranged sets of selection-and-focus field coil and two opposingly arranged pole shoes, since the drive field coils are preferably not arranged adjacent the outer pole shoe segments.

A cross section perpendicular to said inner coil axis through a head portion of said second inner pole shoe segment facing said examination area preferably covers a smaller area than a parallel cross section through a tail portion of said second inner pole shoe segment facing away from said examination area. This increases the gradient field strength obtainable for a given electrical current strength.

In another embodiment the outer diameter of said head portion of the second inner pole shoe segment decreases in the direction of the inner coil axis with decreasing distance from the examination area. This provides a higher magnetic flux density on the surface facing the examination area and thus allows providing higher gradients of the magnetic field within the examination area.

Further, in an embodiment a cross section perpendicular to said inner coil axis through a head portion of said outer pole shoe segments facing said examination area covers a larger area than a parallel cross section through a tail portion of said outer pole shoe segments facing away from said examination area. This measure also contributed to achieving a higher magnetic flux density on the surface facing the examination area.

Another measure contributing to achieving a higher magnetic flux density on the surface facing the examination area is that the distance of the inner diameter of said head portion of the outer pole shoe segments from the inner coil axis decreases in the direction of the inner coil axis with decreasing distance from the examination area.

Preferably, the arrangement of the coils of a set of selection-and-focus field coils is rather flat, wherein said outer coil axes are parallel to each other and to the inner coil axis. This arrangement of the coils is space-saving, relatively easy to manufacture and allows to more easily calculate and/or simulate the achievable magnetic fields.

In an embodiment said selection-and-focus means comprises i1) a first set of selection-and-focus field coils,
i2) at least one second set of selection-and-focus field coils, and
i3) a selection-and-focus field generator unit for generating selection-and-focus field currents to be provided to said first and said sets of selection-and-focus field coils for controlling the generation of said magnetic selection-and-focus field. Preferably, one second set of selection-and-focus field coils arranged on the opposite side of the examination area than said first set of selection-and-focus field coils is used resulting in an apparatus where the examination area is accessible from at least one side. This allows easy positioning of a patient within the examination area, e.g. by just lifting the patient from a transport bed to a patient table arranged in the examination area. This also avoids the need of having many coils arrange coaxially around the examination area so that the examination area has the form of tunnel in between into which the patient has to be moved like in conventional MRI scanners. Patients will thus feel less uncomfortable than in those conventional MRI scanners.

In other embodiments more than two sets of selection-and-focus field coils are provided which are arranged at different angular positions around the examination area. For instance, in case of three sets, they are preferably displaced by an angle of 120° with respect to each other.

Preferably, the selection-and-focus field coils of the first set are identical to the selection-and-focus field coils of the at least one second set. Further, in case of two sets, the various coils of one set are preferably arranged exactly opposite to each respective coils of the other set which also support a more easy calculation of the achievable magnetic fields.

In an embodiment said selection-and-focus field generator unit is configured to generate selection-and-focus field currents individually for each selection-and-focus field coil of said at least one sets of selection-and-focus field coils. This provides the highest flexibility for generating the desired magnetic fields, but also requires the highest number of generator units/channels.

To reduce the number of generator units/channels it is proposed in a preferred embodiment that said selection-and-focus field generator unit is configured to generate selection-and-focus field currents individually for each pair of selection-and-focus field coils of said first and second sets of selection-and-focus field coils, wherein a pair comprises the opposingly arranged selection-and-focus field coils of the two sets.

Another proposal for reducing the number of generator units/channels provides that said selection-and-focus field generator unit is configured to generate selection-and-focus field currents individually for each pair of outer selection-and-focus field coils of said at least one set of selection-and-focus field coils, wherein a pair comprises two opposingly arranged outer selection-and-focus field coils of the same set of selection-and-focus field coils.

Preferably, as mentioned above briefly, the apparatus comprises at least two pole shoes arranged on different sides of said examination area, each pole shoe having a number of pole shoe segments carrying the various selection-and-focus field coils and a pole shoe yoke connecting said pole shoe segments.

To shield the at least one set of selection-and-focus field coils from magnetic fields generated by the drive field coils an inner surface of said at least one set of selection-and-focus field coils facing said examination area is covered by a shielding. This shielding particularly prevents a disturbance of the measurement signal, which would occur if the drive field interacts with the soft-magnetic material.

As mentioned above said drive field coils are arranged in the area between said first inner selection-and-focus field coils of the twos sets of selection-and-focus field coils. The drive field coils may be designed such that they are (fixedly or movable) arranged between the two sets of selection-and-focus field coils. In other embodiments, the drive field coils are somewhat flexible and can be arranged on the desired portion of the patient's body before the patient is placed inside the examination area.

Preferably, said drive field coils are smaller in a direction perpendicular to the inner coil axis than the distance in said direction between to opposing outer selection-and-focus field coils. Further, preferably, said drive field coils comprises two pairs of saddle coils arranged around a central symmetry axis perpendicular to said inner coil axis and a solenoid coil arranged around said central symmetry axis.

In another preferred embodiment said drive field signal generator unit is adapted for generating and providing individual drive field currents to one or more of said drive field coils. Further, in an embodiment said drive field signal generator unit is adapted for generating drive field current in dependence on the sensitivity and/or position of the first sub-zone or the field of view within the examination area. These measures allow to reduce the SAR (specific absorption rate) and the PNS (peripheral nerve stimulation), which is particularly important for a human-size apparatus, and to reduce the dissipated average power in the drive field coils leading to cost savings.

For receiving detection signals need for determining the distribution of magnetic particles within the examination area and, thus, for generating images of the examination area, e.g. of the heart region of a patient, the apparatus further comprises a receiving means comprising at least one signal receiving unit and at least one receiving coil for acquiring detection signals, which detection signals depend on the magnetization in the field of view, which magnetization is influenced by the change in the position in space of the first and second sub-zone.

In a preferred embodiment the one or more inner pole shoe segments and/or the outer one or more pole shoe segments comprise two or more parts having different cross sections, in particular different forms (e.g. cylindrical, elliptical, rectangular, etc.), different diameters and/or different symmetry axes.

In a preferred embodiment an inner pole shoe segment (preferably all inner pole shoe segments) comprises an inner cylinder and an outer ring arranged around the inner cylinder. Preferably, a first coil is arranged between the inner cylinder and the outer ring and a second coil is arranged around the outer ring.

Further, in an embodiment, the outer ring comprises two or more parts, wherein in a lower part facing away from the opposing pole shoe the outer diameter is larger than in an upper part facing the opposing pole shoe.

In a preferred embodiment an outer pole shoe segment (preferably all outer pole shoe segments) comprises a lower part facing away from the opposing pole shoe having a different cross section than an upper part facing the opposing pole shoe. Preferably, the lower part has a circular cross section whereas the upper part has an elliptical cross section. Further, in an embodiment the lower part is arranged at a larger distance from the inner pole shoe segment than the upper part.

Preferably, a single coil or two or more coils coupled in series are arranged around both the upper and the lower parts of an outer pole shoe segment. In another embodiment, only around the lower pole shoe segment a coil is arranged.

In a preferred embodiment a pole shoe comprises a group of inner pole shoe segments, in particular three or four inner pole shoe segments, preferably arranged in an array (e.g. a triangle or square).

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 3. In particular, two embodiments of an MPI scanner for medical diagnostics will be described. An informal description of the data acquisition will also be given. The similarities and differences between the two embodiments will be pointed out.

Figure 1:
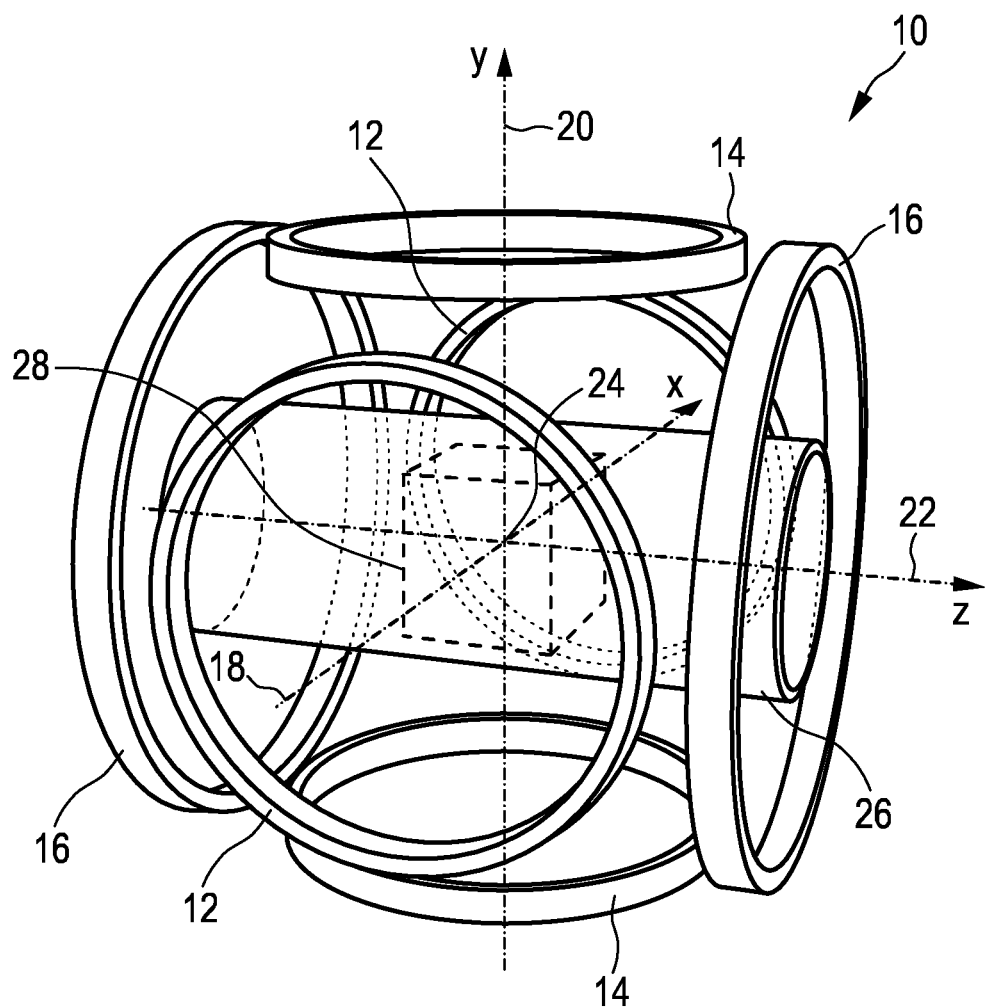
FIG. 1 shows a first embodiment of an MPI apparatus.

The first embodiment 10 of an MPI scanner shown in FIG. 1 has three pairs 12, 14, 16 of coaxial parallel circular coils, these coil pairs being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x- and z-axes are horizontal. The coil pairs 12, 14, 16 are named after their axes. For example, the y-coil pair 14 is formed by the coils at the top and the bottom of the scanner. Moreover, the coil with the positive (negative) y-coordinate is called the $y^+$-coil ($y^-$-coil), and similarly for the remaining coils. When more convenient, the coordinate axes and the coils shall be labelled with $x_1$, $x_2$, and $x_3$, rather than with x, y, and z.

The scanner 10 can be set to direct a predetermined, time-dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the $z^+$-coil, and the current $-I^S$ is made to flow through the $z^-$-coil. The z-coil pair 16 then acts as an anti-parallel circular coil pair.

It should be noted here that the arrangement of the axes and the nomenclature given to the axes in this embodiment is just an example and might also be different in other embodiments. For instance, in practical embodiments the vertical axis is often considered as the z-axis rather than the y-axis as in the present embodiment. This, however, does not generally change the function and operation of the device and the effect of the present invention.

Figure 2:
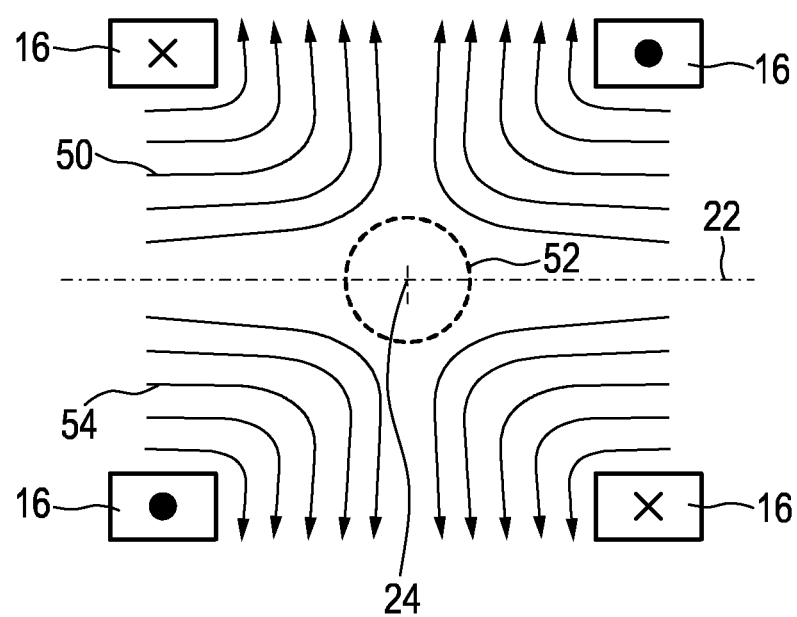
FIG. 2 shows an example of the selection field pattern produced by an apparatus as shown in FIG. 1.

The magnetic selection field, which is generally a magnetic gradient field, is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 (including the field-free point) within the field of view 28 the (overall) magnetization in the field of view 28 changes. By determining the magnetization in the field of view 28 or physical parameters influenced by the magnetization, information about the spatial distribution of the magnetic particles in the field of view 28 can be obtained. In order to change the relative spatial position of the two sub-zones 52, 54 (including the field-free point) in the field of view 28, further magnetic fields, i.e. the magnetic drive field, and, if applicable, the magnetic focus field, are superposed to the selection field 50.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field (of course, in other embodiments, separate coils may be provided). The current flowing through the $z^\pm$-coil is $I^D_3 + I^F_3 \pm I^S$. The current flowing through the remaining two coil pairs 12, 14 is $I^D_k + I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field-free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time-dependent. The difference between the focus field and the drive field is that the focus field varies slowly in time and may have a large amplitude, while the drive field varies rapidly and has a small amplitude. There are physical and biomedical reasons to treat these fields differently. A rapidly varying field with a large amplitude would be difficult to generate and potentially hazardous to a patient.

In a practical embodiment the FFP can be considered as a mathematical point, at which the magnetic field is assumed to be zero. The magnetic field strength increases with increasing distance from the FFP, wherein the increase rate might be different for different directions (depending e.g. on the particular layout of the device). As long as the magnetic field strength is below the field strength required for bringing magnetic particles into the state of saturation, the particle actively contributes to the signal generation of the signal measured by the device; otherwise, the particles are saturated and do not generate any signal.

The embodiment 10 of the MPI scanner has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair. The receive coils are supposed to be well decoupled. The time-dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from zero Hertz ("DC") up to the frequency where the expected signal level drops below the noise level. Alternatively, the MPI scanner has no dedicated receive coils. Instead the drive field transmit coils are used as receive coils.

The embodiment 10 of the MPI scanner shown in FIG. 1 has a cylindrical bore 26 along the z-axis 22, i.e. along the axis of the selection field. All coils are placed outside this bore 26. For the data acquisition, the patient (or object) to be imaged is placed in the bore 26 such that the patient's volume of interest—that volume of the patient (or object) that shall be imaged—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, a cylinder or an arbitrary shape. A cubical field of view 28 is illustrated in FIG. 1.

The size of the first sub-zone 52 is dependent on the strength of the gradient of the magnetic selection field and on the field strength of the magnetic field required for saturation, which in turn depends on the magnetic particles. For a sufficient saturation of typical magnetic particles at a magnetic field strength of 80 A/m and a gradient (in a given space direction) of the field strength of the magnetic selection field amounting to $50 \times 10^3$ A/m$^2$, the first sub-zone 52 in which the magnetization of the particles is not saturated has dimensions of about 1 mm (in the given space direction).

The patient's volume of interest is supposed to contain magnetic nanoparticles. Prior to the diagnostic imaging of, for example, a tumor, the magnetic particles are brought to the volume of interest, e.g. by means of a liquid comprising the magnetic particles which is injected into the body of the patient (object) or otherwise administered, e.g. orally, to the patient.

Generally, various ways for bringing the magnetic particles into the field of view exist. In particular, in case of a patient into whose body the magnetic particles are to be introduced, the magnetic particles can be administered by use of surgical and non-surgical methods, and there are both methods which require an expert (like a medical practitioner) and methods which do not require an expert, e.g. can be carried out by laypersons or persons of ordinary skill or the patient himself/herself. Among the surgical methods there are potentially non-risky and/or safe routine interventions, e.g. involving an invasive step like an injection of a contrast agent into a blood vessel (if such an injection is at all to be considered as a surgical method), i.e. interventions which do not require considerable professional medical expertise to be carried out and which do not involve serious health risks. Further, non-surgical methods like swallowing or inhalation can be applied.

Generally, the magnetic particles are pre-delivered or pre-administered before the actual steps of data acquisition are carried out. In embodiments, it is, however, also possible that further magnetic particles are delivered/administered into the field of view.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 µm with such magnetic particles, a magnetic field of approximately 800 A/m (corresponding approximately to a flux density of 1 mT) is then required, whereas in the case of a diameter of 100 µm a magnetic field of 80 A/m suffices. Even smaller values are obtained when a coating of a material having a lower saturation magnetization is chosen or when the thickness of the layer is reduced.

In practice, magnetic particles commercially available under the trade name Resovist (or similar magnetic particles) are often used, which have a core of magnetic material or are formed as a massive sphere and which have a diameter in the range of nanometers, e.g. 40 or 60 nm.

For further details of the generally usable magnetic particles and particle compositions, the corresponding parts of EP 1304542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

During the data acquisition, the x-, y-, and z-coil pairs 12, 14, 16 generate a position- and time-dependent magnetic field, the applied field. This is achieved by directing suitable currents through the field generating coils. In effect, the drive and focus fields push the selection field around such that the FFP moves along a preselected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time-dependent voltage $V_k$ across the terminals of the receive coil pair along the $x_k$-axis. The associated receiver converts this voltage to a signal $S_k$, which it processes further.

Figure 3:
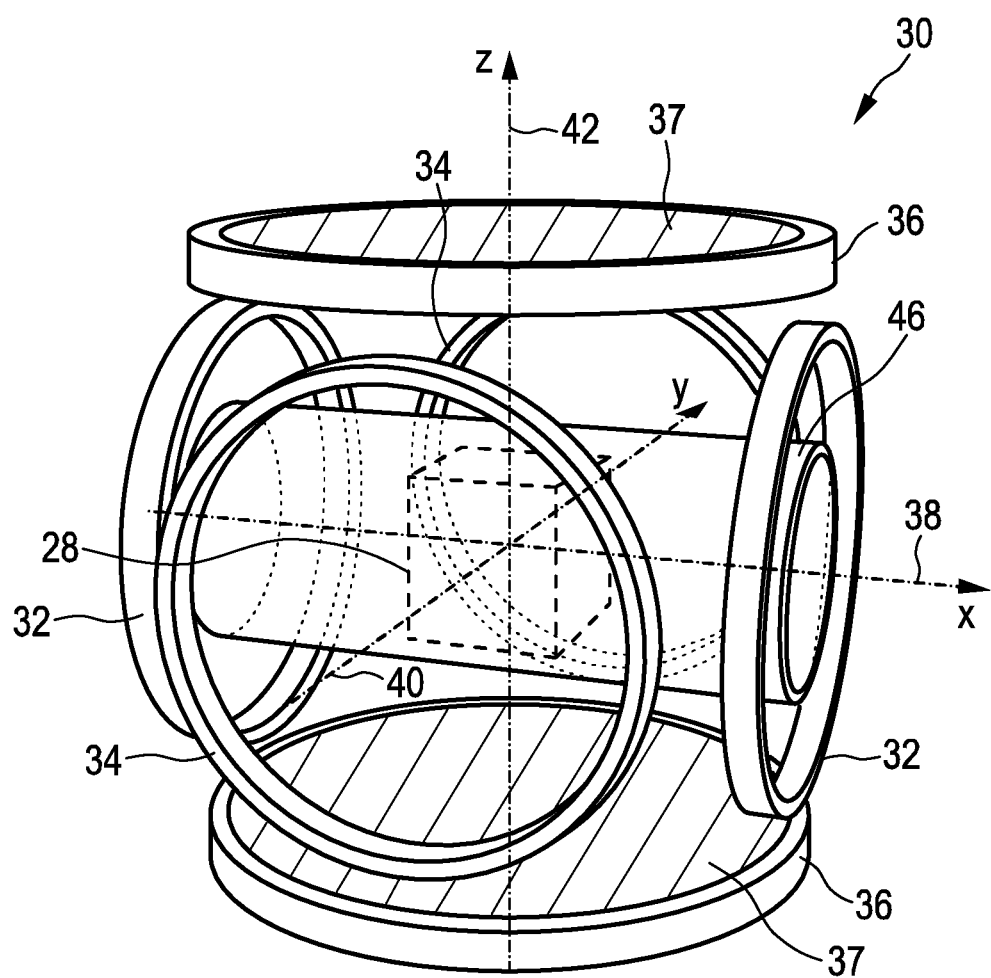
FIG. 3 shows a second embodiment of an MPI apparatus.

Like the first embodiment 10 shown in FIG. 1, the second embodiment 30 of the MPI scanner shown in FIG. 3 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The drive field is generated by a solenoid (not shown) along the x-axis 38 and by pairs of saddle coils (not shown) along the two remaining axes 40, 42. These coils are wound around a tube which forms the bore. The drive field coils also serve as receive coils.

To give a few typical parameters of such an embodiment: The z-gradient of the selection field, G, has a strength of $G/\mu_0=2.5$ T/m, where $\mu_0$ is the vacuum permeability. The temporal frequency spectrum of the drive field is concentrated in a narrow band around 25 kHz (up to approximately 150 kHz). The useful frequency spectrum of the received signals lies between 50 kHz and 1 MHz (eventually up to approximately 15 MHz). The bore has a diameter of 120 mm. The biggest cube 28 that fits into the bore 46 has an edge length of 120 mm/$\sqrt{2}$≈84 mm.

Since the construction of field generating coils is generally known in the art, e.g. from the field of magnetic resonance imaging, this subject need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

Figure 4A:
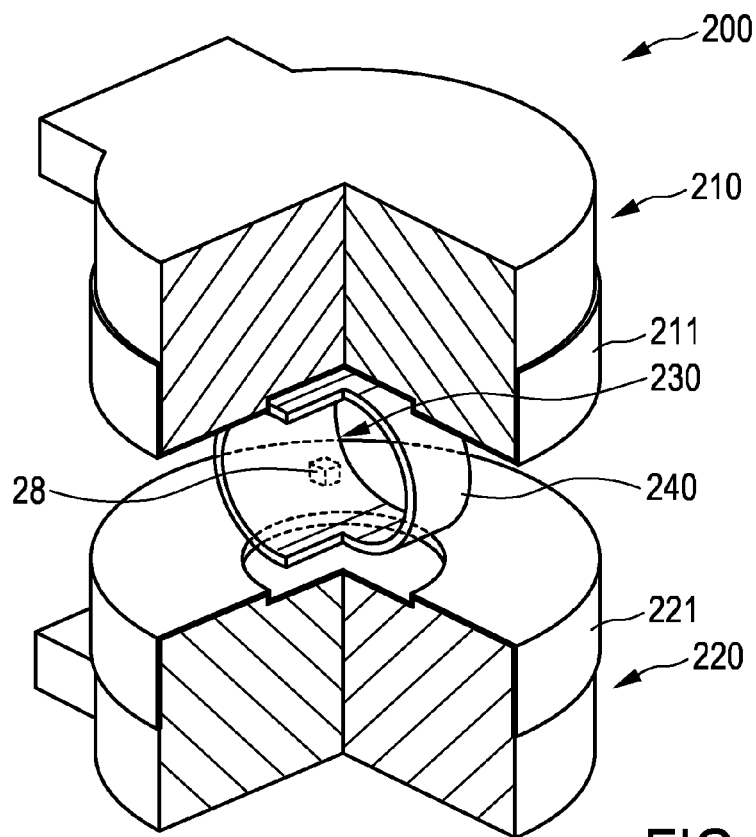
FIG. 4 shows two embodiments of the general outer layout of an MPI apparatus according to the present invention.

FIG. 4 shows two embodiments of the general outer layout of an MPI apparatus 200, 300 according to the present invention. FIG. 4A shows an embodiment of the proposed MPI apparatus 200 comprising two selection-and-focus field coil units 210, 220 which are basically identical and arranged on opposite sides of the examination area 230 formed between them. Further, a drive field coil unit 240 is arranged between the selection-and-focus field coil units 210, 220, which are placed around the area of interest of the patient (not shown). The selection-and-focus field coil units 210, 220 comprise several selection-and-focus field coils for generating a combined magnetic field representing the above-explained magnetic selection field and magnetic focus field. In particular, each selection-and-focus field coil unit 210, 220 comprises a, preferably identical, set of selection-and-focus field coils. Details of said selection-and-focus field coils will be explained below.

The drive field coil unit 240 comprises a number of drive field coils for generating a magnetic drive field. These drive field coils may comprise several pairs of drive field coils, in particular one pair of drive field coils for generating a magnetic field in each of the three directions in space. In an embodiment the drive field coil unit 240 comprises two pairs of saddle coils for two different directions in space and one solenoid coil for generating a magnetic field in the longitudinal axis of the patient.

The selection-and-focus field coil units 210, 220 are generally mounted to a holding unit (not shown) or the wall of room. Preferably, in case the selection-and-focus field coil units 210, 220 comprise pole shoes for carrying the respective coils, the holding unit does not only mechanically hold the selection-and-focus field coil unit 210, 220 but also provides a path for the magnetic flux that connects the pole shoes of the two selection-and-focus field coil units 210, 220.

As shown in FIG. 4a, the two selection-and-focus field coil units 210, 220 each include a shielding layer 211, 221 for shielding the selection-and-focus field coils from magnetic fields generated by the drive field coils of the drive field coil unit 240.

Figure 4B:
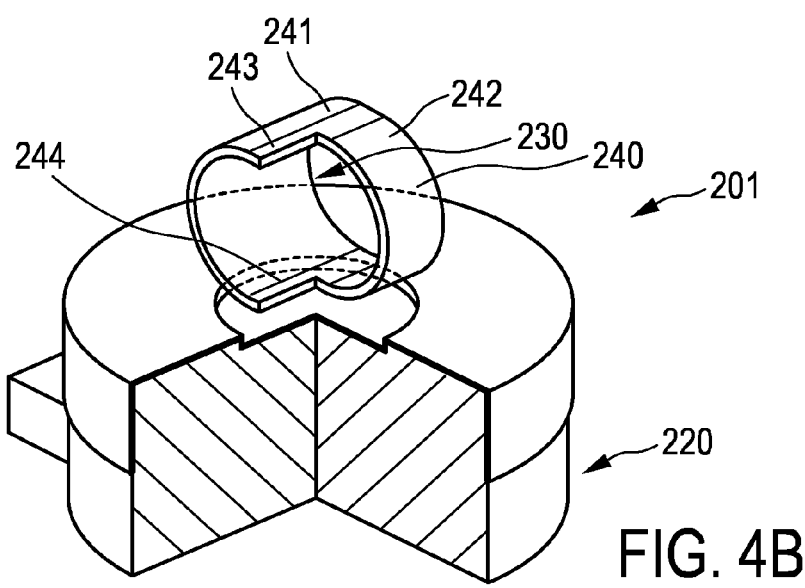

In the embodiment of the MPI apparatus 201 shown in FIG. 4B only a single selection-and-focus field coil unit 220 is provided as well as the drive field coil unit 240. Generally, a single selection-and-focus field coil unit is sufficient for generating the required combined magnetic selection and focus field. Said single selection-and-focus field coil unit 220 may thus be integrated into a (not shown) patient table on which a patient is placed for the examination. Preferably, the drive field coils of the drive field coil unit 240 may be arranged around the patient's body already in advance, e.g. as flexible coil elements. In another implementation, the drive field coil unit 240 can be opened, e.g. separable into two subunits 241, 242 as indicated by the separation lines 243, 244 shown in FIG. 4B in axial direction, so that the patient can be placed in between and the drive field coil subunits 241, 242 can then be coupled together.

In still further embodiments of the MPI apparatus, even more selection-and-focus field coil units may be provided which are preferably arranged according to a uniform distribution around the examination area 230. However, the more selection-and-focus field coil units are used, the more will the accessibility of the examination area for placing a patient therein and for accessing the patient itself during an examination by medical assistance or doctors be limited.

Figure 5:
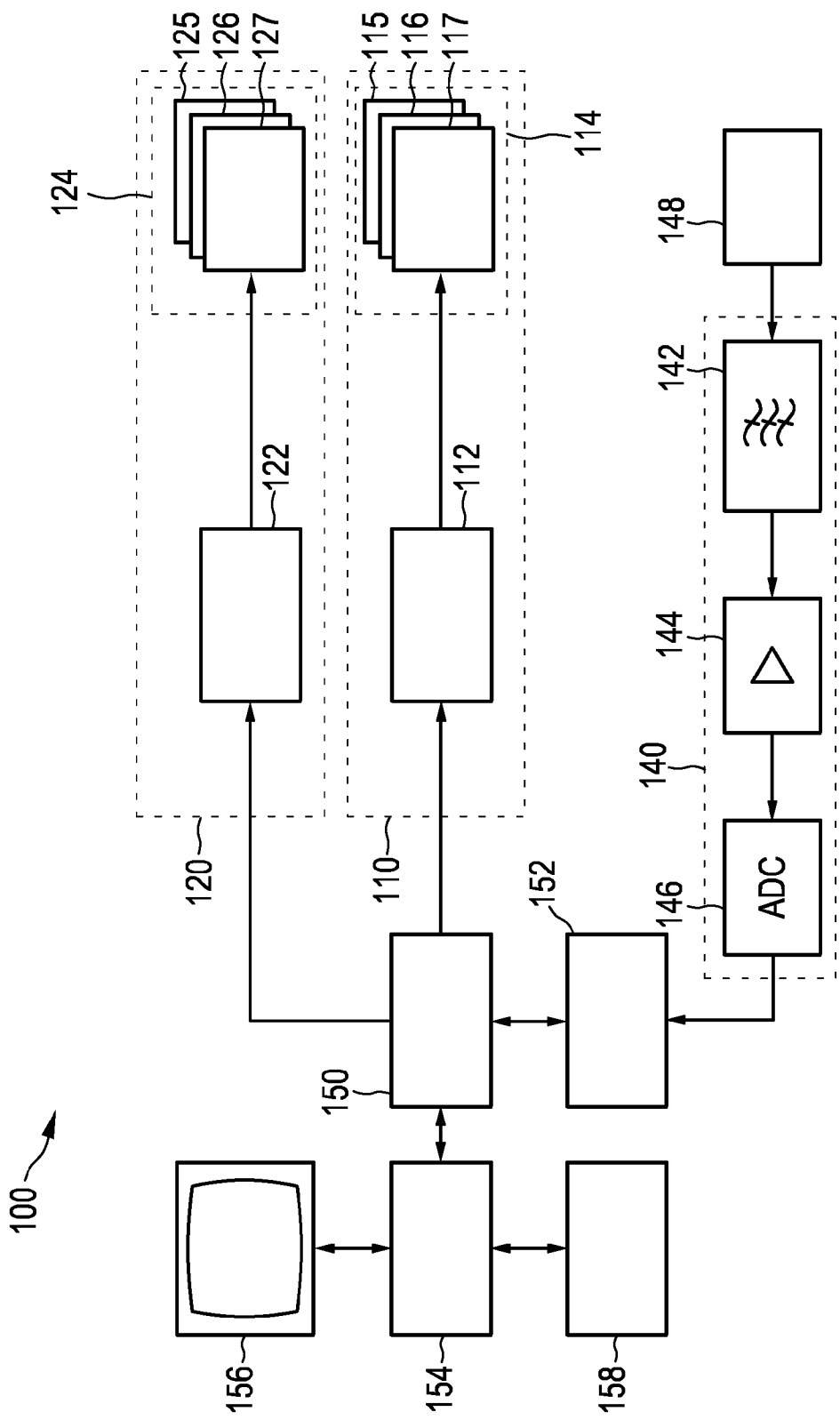
FIG. 5 shows a block diagram of an MPI apparatus according to the present invention.

FIG. 5 shows a general block diagram of an MPI apparatus 100 according to the present invention. The general principles of magnetic particle imaging explained above are valid and applicable to this embodiment as well, unless otherwise specified.

The embodiment of the apparatus 100 shown in FIG. 5 comprises various coils for generating the desired magnetic fields. First, the coils and their functions in MPI shall be explained.

For generating the combined magnetic selection-and-focus field, selection-and-focus means 110 are provided. The magnetic selection-and-focus field has a pattern in space of its magnetic field strength such that the first sub-zone (52 in FIG. 2) having a low magnetic field strength where the magnetization of the magnetic particles is not saturated and a second sub-zone (54 in FIG. 4) having a higher magnetic field strength where the magnetization of the magnetic particles is saturated are formed in the field of view 28, which is a small part of the examination area 230, which is conventionally achieved by use of the magnetic selection field. Further, by use the magnetic selection-and-focus field the position in space of the field of view 28 within the examination area 230 can be changed, as conventionally done by use of the magnetic focus field.

The selection-and-focus means 110 comprises at least one set of selection-and-focus field coils 114 and a selection-and-focus field generator unit 112 for generating selection-and-focus field currents to be provided to said at least one set of selection-and-focus field coils 114 (representing one of the selection-and-focus field coil units 210, 220 shown in FIGS. 4A, 4B) for controlling the generation of said magnetic selection-and-focus field. Preferably, a separate generator subunit is provided for each coil element (or each pair of coil elements) of the at least one set of selection-and-focus field coils 114. Said selection-and-focus field generator unit 112 comprises a controllable current source (generally including an amplifier) and a filter unit which provide the respective coil element with the field current to individually set the gradient strength and field strength of the contribution of each coil to the magnetic selection-and-focus field. It shall be noted that the filter unit 114 can also be omitted.

For generating the magnetic drive field the apparatus 100 further comprises drive means 120 comprising a drive field signal generator unit 122 and a set of drive field coils 124 (representing the drive coil unit 240 shown in FIGS. 4A, 4B) for changing the position in space and/or size of the two sub-zones in the field of view by means of a magnetic drive field so that the magnetization of the magnetic material changes locally. As mentioned above said drive field coils 124 preferably comprise two pairs 125, 126 of oppositely arranged saddle coils and one solenoid coil 127. Other implementations, e.g. three pairs of coil elements, are also possible.

The drive field signal generator unit 122 preferably comprises a separate drive field signal generation subunit for each coil element (or at least each pair of coil elements) of said set of drive field coils 124. Said drive field signal generator unit 122 preferably comprises a drive field current source (preferably including a current amplifier) and a filter unit (which may also be omitted with the present invention) for providing a time-dependent drive field current to the respective drive field coil.

The selection-and-focus field signal generator unit 112 and the drive field signal generator unit 122 are preferably controlled by a control unit 150, which preferably controls the selection-and-focus field signal generator unit 112 such that the sum of the field strengths and the sum of the gradient strengths of all spatial points of the selection field is set at a predefined level. For this purpose the control unit 150 can also be provided with control instructions by a user according to the desired application of the MPI apparatus, which, however, is preferably omitted according to the present invention.

For using the MPI apparatus 100 for determining the spatial distribution of the magnetic particles in the examination area (or a region of interest in the examination area), particularly to obtain images of said region of interest, signal detection receiving means 148, in particular a receiving coil, and a signal receiving unit 140, which receives signals detected by said receiving means 148, are provided. Preferably, three receiving coils 148 and three receiving units 140—one per receiving coil—are provided in practice, but more than three receiving coils and receiving units can be also used, in which case the acquired detection signals are not 3-dimensional but K-dimensional, with K being the number of receiving coils.

Said signal receiving unit 140 comprises a filter unit 142 for filtering the received detection signals. The aim of this filtering is to separate measured values, which are caused by the magnetization in the examination area which is influenced by the change in position of the two part-regions (52, 54), from other, interfering signals. To this end, the filter unit 142 may be designed for example such that signals which have temporal frequencies that are smaller than the temporal frequencies with which the receiving coil 148 is operated, or smaller than twice these temporal frequencies, do not pass the filter unit 142. The signals are then transmitted via an amplifier unit 144 to an analog/digital converter 146 (ADC).

The digitalized signals produced by the analog/digital converter 146 are fed to an image processing unit (also called reconstruction means) 152, which reconstructs the spatial distribution of the magnetic particles from these signals and the respective position which the first part-region 52 of the first magnetic field in the examination area assumed during receipt of the respective signal and which the image processing unit 152 obtains from the control unit 150. The reconstructed spatial distribution of the magnetic particles is finally transmitted via the control means 150 to a computer 154, which displays it on a monitor 156. Thus, an image can be displayed showing the distribution of magnetic particles in the field of view of the examination area.

In other applications of the MPI apparatus 100, e.g. for influencing the magnetic particles (for instance for a hyperthermia treatment) or for moving the magnetic particles (e.g. attached to a catheter for moving the catheter or attached to a medicament for moving the medicament to a certain location) the receiving means may also be omitted or simply not used.

Further, an input unit 158 may optionally be provided, for example a keyboard. A user may therefore be able to set the desired direction of the highest resolution and in turn receives the respective image of the region of action on the monitor 156. If the critical direction, in which the highest resolution is needed, deviates from the direction set first by the user, the user can still vary the direction manually in order to produce a further image with an improved imaging resolution. This resolution improvement process can also be operated automatically by the control unit 150 and the computer 154. The control unit 150 in this embodiment sets the gradient field in a first direction which is automatically estimated or set as start value by the user. The direction of the gradient field is then varied stepwise until the resolution of the thereby received images, which are compared by the computer 154, is maximal, respectively not improved anymore. The most critical direction can therefore be found respectively adapted automatically in order to receive the highest possible resolution.

Figure 6A:
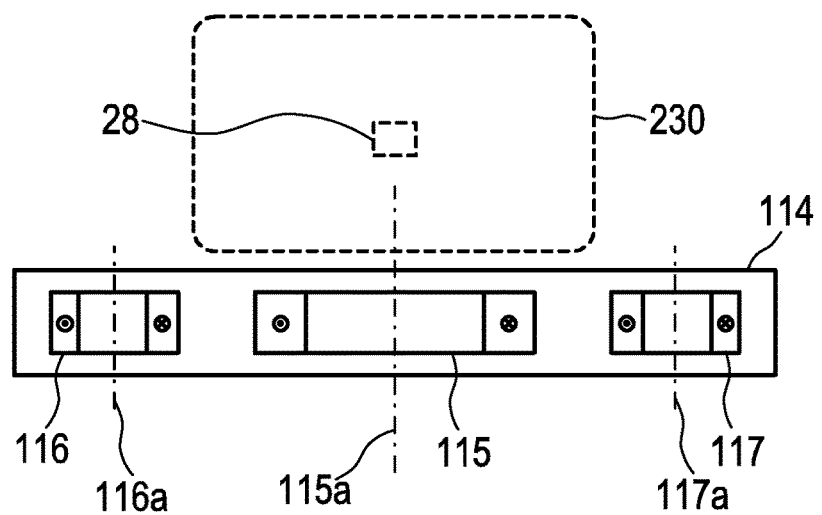
FIG. 6 shows two perpendicular cross sections through an embodiment of a selection-and-focus field coil arrangement according to the present invention.
Figure 6B:
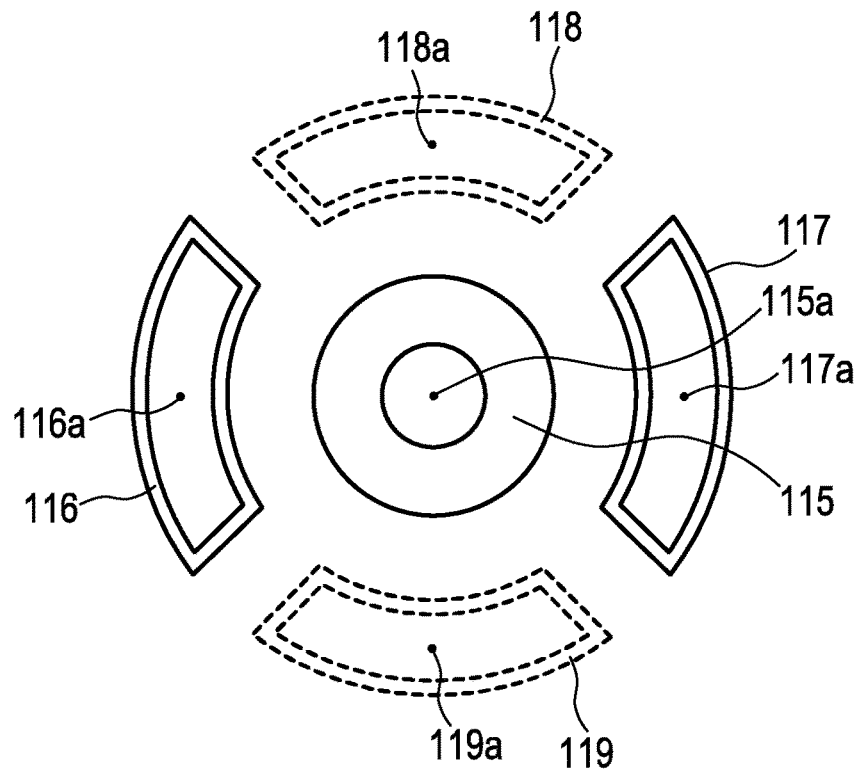

According to the present invention said selection-and-focus field coils 114 comprise at least one inner selection-and-focus field coil 115 being formed as a closed loop about an inner coil axis 115a, and a group of at least two outer selection-and-focus field coils 116, 117 arranged at a larger distance from said inner coil axis 115a than said at least one inner selection-and-focus field coil 115 and at different angular positions, each being formed as a closed loop about an associated outer coil axis 116a, 117a as shown in FIGS. 6A and 6B showing perpendicular cross sections. Preferably, two additional outer selection-and-focus field coils 118, 119, each being formed as a closed loop about an associated outer coil axis 118a, 119a are provided as indicated by the dashed lines in FIG. 6B.

It is generally possible according to the present invention that the selection-and-focus field means only comprises various coils as shown in FIG. 6. However, it is preferred according to the present invention that the selection-and-focus field means are a combination of magnetic material in the form of one or more pole shoes, particularly soft-magnetic material, and electromagnetic coils. The at least one pole shoe serves for conducting the magnetic flux and, thus, for increasing the generation of the required magnetic fields.

Figure 7A:
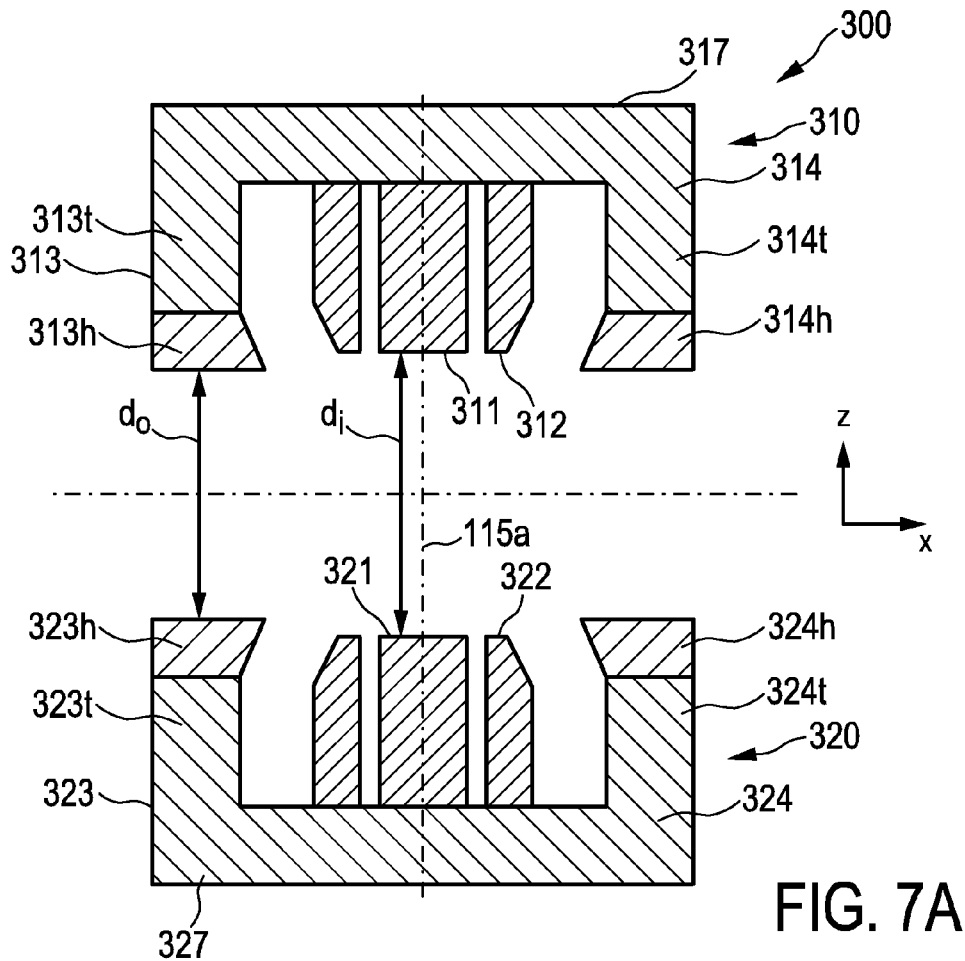
FIG. 7 shows two perpendicular cross sections through an embodiment of a pole shoe arrangement according to the present invention.
Figure 7B:
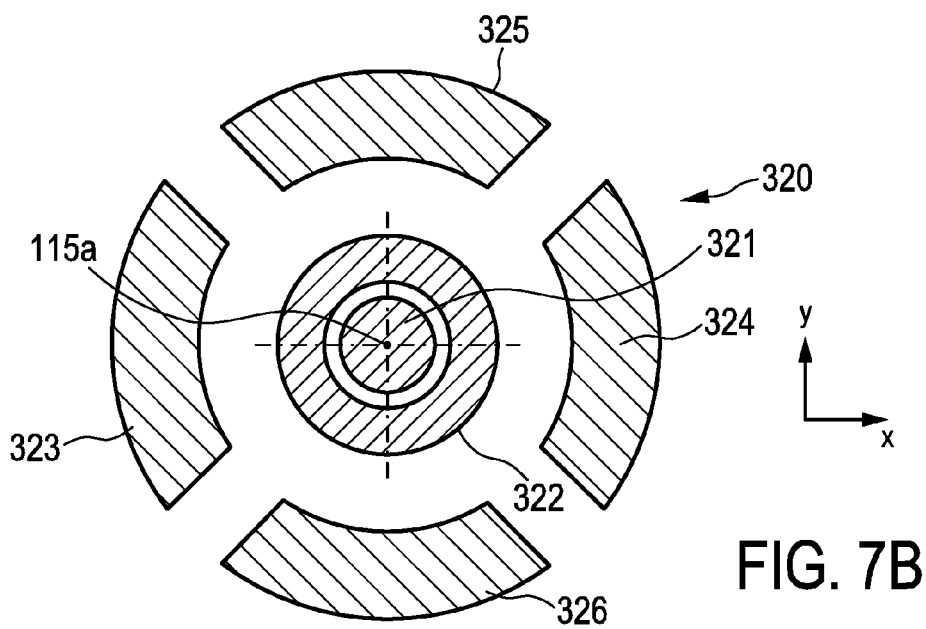
Figure 8:
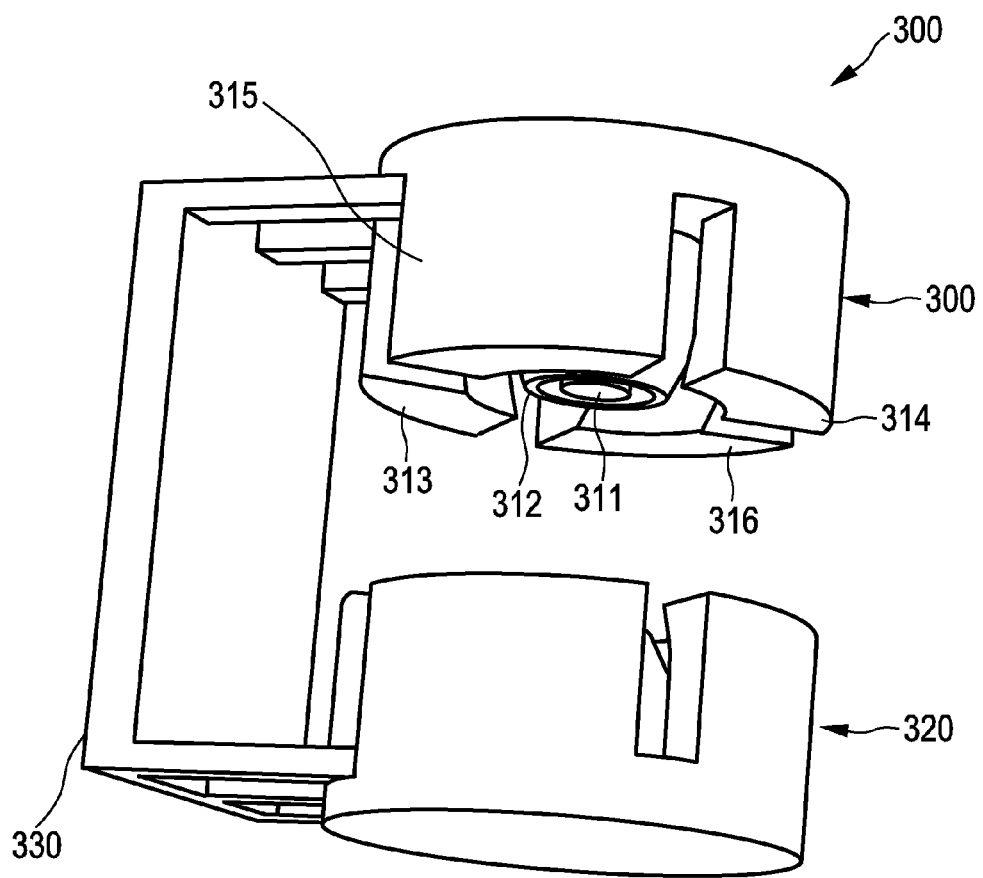
FIG. 8 shows a perspective view of the embodiment of a pole shoe arrangement according to the present invention shown in FIG. 7.

An embodiment of a pole shoe arrangement according to the present invention is shown in FIGS. 7 and 8, wherein FIGS. 7A and 7B show two perpendicular cross sections through the pole shoe arrangement 300 and FIG. 8 shows a perspective view of the pole shoe arrangement 300. In this embodiment of the pole shoe arrangement 300 two pole shoes 310, 320 are provided which are connected via a pole shoe bearing 330 mechanically carrying and magnetically coupling the two pole shoes 310, 320. While the pole shoes 310, 320 shown in these figures will, in this embodiment, have the geometrical properties shown here, the particular shape of the pole shoe bearing 330 is only shown here as a simple example, while the particular shape for a practical application will be determined by construction parameters like the required stability.

As shown in FIGS. 7 and 8 each pole shoe 310, 320 comprises at least one, here in this embodiment two, inner pole shoe segments 311, 312 and 321, 322, respectively, and at least two, here in this embodiment four, outer pole shoe segments 313-316 and 323-326, respectively. Further, each pole shoe 310, 320 comprises a pole shoe yoke 317 and 327, respectively, that connects the various pole shoe segments of the same pole shoe.

All pole shoe segments of a common pole shoe are coaxially arranged about the common inner coil axis 115a wherein the second inner pole shoe segments 312, 322 are arranged as rings around the respective inner pole shoe segment 311, 321. The outer pole shoe segments 313-316 and 323-326, respectively, are each designed in form of a ring segment arranged at the same distance around the inner coil axis 115a but have different angular positions as shown in FIG. 7B.

Such an arrangement of pole shoes, on which the various coils of the selection-and-focus field coils are arranged as will be shown and explained below, is advantageous for achieving the desired movement of the selection-and-focus field coil (the first sub-zone 52). The segmentation of the outer pole shoe segments, here in two to four segments (generally at least two segments, but also more segments are possible), is particularly advantageous for movement of the FFP along the x- and y-direction.

In a practical implementation, the distance $d_i$ between the inner pole shoe segments 311, 321 (in z-direction) is at least so large that a patient as well as drive field coils can be arranged there between. This means that the distance $d_i$ should be at least 40 cm, preferably at least 45 cm. The distance $d_o$ between the outer pole shoe segments b can be slightly smaller since there between no drive field coils are generally arranged. Hence, the distance $d_o$ should be at least 25 cm, preferably at least 40 cm.

The pole shoes are generally made of soft-magnetic material. Preferably, the two inner pole shoe segments 311, 312 and 321, 322, respectively, and head portions 313h-314h and 323h-324h (see FIG. 7A; the head portions of the other outer pole shoe segments are not explicitly shown in this figure) are made from a soft-magnetic material and have a high saturation induction, in particular FeCo, Fe, Dy, Gd or an alloy thereof such as $Fe_{49}V_{1.9}Co_{49}$ (such as the material known under the trade name Vacoflux48). Alternatively, FeNi may be used, but this material has a lower saturation induction. Preferably, the tail portions 313t, 314t and 323t, 324t of the outer pole shoe segments (the tail portions of the outer pole shoe segments 315 or 316, 325, 326 are not explicitly shown) facing away from the examination area and the pole shoe yoke are made from the same material. However, for cost reasons it is possible to make them from a soft-magnetic material having a lower saturation induction than the material of the inner head pole shoe segments, in particular FeSi, FeNi, Permalloy or an alloy thereof such as $Fe_{73.5}Cu_1Nb_3Si_{15.5}B_7$ (commonly known as Nanoperm).

Figure 9A:
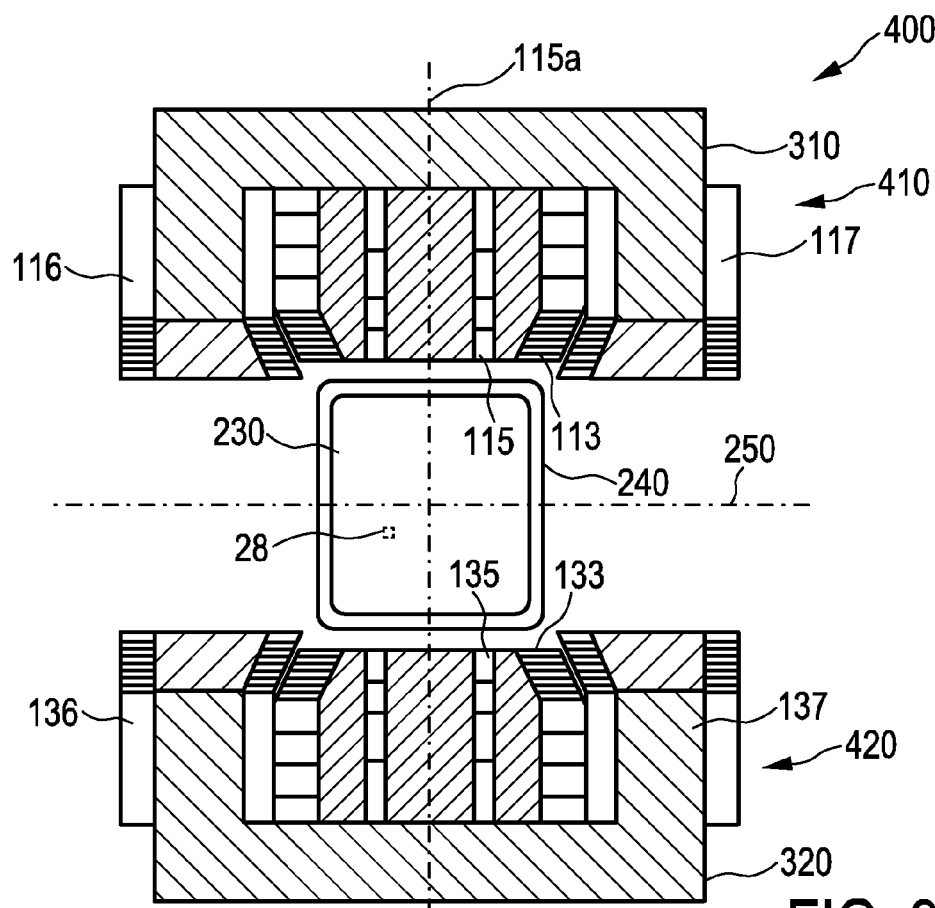
FIG. 9 shows two perpendicular cross sections through an embodiment of a selection-and-focus field coil arrangement according to the present invention.
Figure 9B:
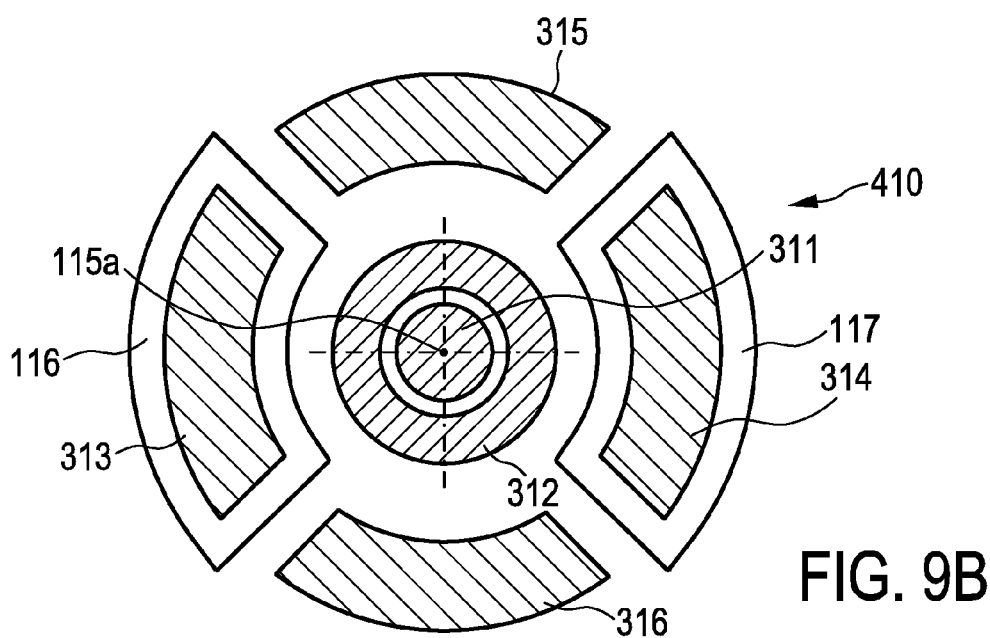

FIG. 9 shows two perpendicular cross sections through an embodiment of a selection-and-focus field coil arrangement 400 according to the present invention in which the various selection-and-focus field coils are mounted on a pole shoe arrangement 300 as shown in FIGS. 7 and 8.

Figure 10:
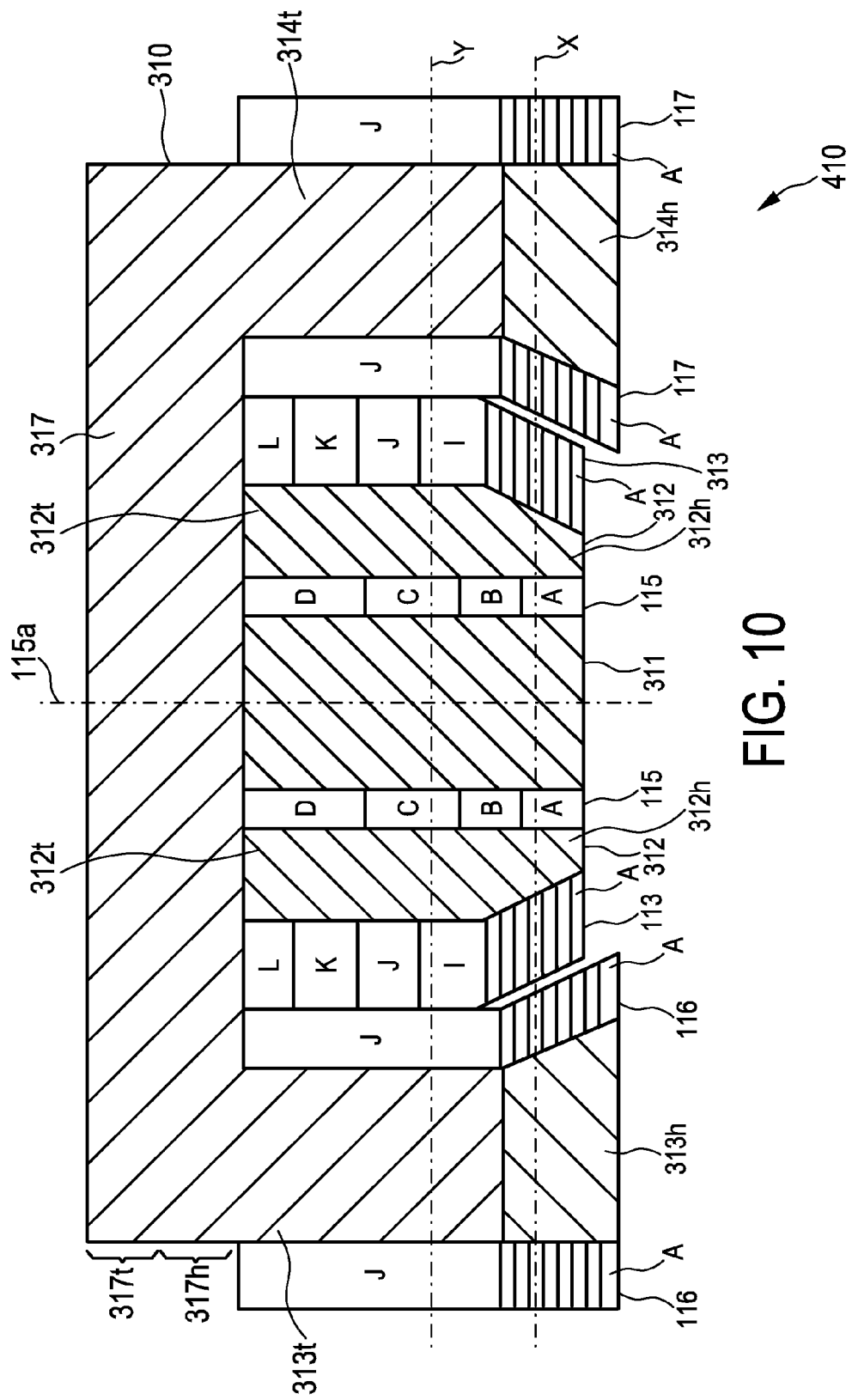
FIG. 10 shows an enlarged of one of the cross sections through an embodiment of one set of selection-and-focus field coils of the selection-and-focus field coil arrangement shown in FIG. 9.

FIG. 10 shows an enlarged view of a single selection-and-focus field coil sub-unit 410 which will be used to explain further details thereof. The first inner pole shoe segment 311 carries the first inner selection-and-focus field coil 115 which is formed as a ring around said first inner pole shoe segment 311. A second inner selection-and-focus field coil 113 is formed as another ring coil which is carried by the second inner pole shoe segment 312, which itself is formed as a ring around said first inner selection-and-focus field coil 115. Four outer selection-and-focus field coils 116, 117 (only two outer selection-and-focus field coils are shown in FIGS. 9 and 10; the other two outer selection-and-focus field coils are not shown in FIGS. 9 and 10) are carried by respective outer pole shoe segments 313, 314, 315, 316. Each of said outer selection-and-focus field coils 116, 117 is wound around its associated outer pole shoe segment 313, 314, 315, 316 so that the current flows around the respective outer pole show segment. Each outer pole shoe segment 313, 314, 315, 316 has the form of a ring segment arranged at different angular positions around the inner coil axis 115a.

Thus, the selection-and-focus field coil arrangement 400 shown in FIG. 9A comprises in total twelve selection-and-focus field coils, six coils (the coils 113, 115-119) in the upper selection-and-focus field coil sub-unit 410 and six coils (the coils 133, 135, 136; the remaining two coils are not visible in FIG. 9A) in the lower selection-and-focus field coil sub-unit 420. This number shall, however, only be understood as an exemplary number. Other numbers are possible as well. Generally, at least six, preferably at least eight, selection-and-focus field coil units are desired.

Preferably, for each selection-and-focus field coil a single selection-and-focus field generator sub-unit is provided so that each selection-and-focus field coil can be individually controlled by providing an individual current to the selection-and-focus field coil. However, it is also possible to couple selection-and-focus field coils together and provide them with a common current so that the number of selection-and-focus field generator sub-units can be reduced. For instance, in an embodiment the two outer selection-and-focus field coils 116 and 117 are provided by a common current. Similarly, the other two outer selection-and-focus field coils are coupled together. This means that for such an selection-and-focus field coil arrangement in total eight selection-and-focus field generator sub-units are required.

In another embodiment, the two oppositely arranged selection-and-focus field coils of two different selection-and-focus field coil sub-units 410, 420 are coupled together and provided with a common current. For instance, the two (in FIG. 9) outer selection-and-focus field coils on the right-hand side may be coupled together and be provided with the identical current. The same holds for the other outer selection-and-focus field coils.

Preferably, according to an embodiment of the present invention one or more of the selection-and-focus field coils are split into at least two, in particular at least four, coil segments, wherein coil segments of a coil are arranged adjacent to each other in the direction of the associated coil axis (which means, in the direction of the inner coil axis 115a if all coil axes are parallel as in the depicted embodiment) and wherein adjacent coil segments are electrically connected. Preferably, as shown in FIGS. 9 and 10, all selection-and-focus field coils are split into several coil segments as indicated by multiple coil sample division lines in FIGS. 9A and 10.

For instance, the first inner selection-and-focus field coil 115 is split into four coil segments indicated by letters A, B, C, D in FIG. 10. Similarly, the second inner selection-and-focus field coil 113 and the various outer selection-and-focus field coils 116, 117 are split into a plurality of coil segments indicated by letters A, B, C, etc.

This splitting of the selection-and-focus field coils into several segments enables the realization of different current densities along the respective selection-and-focus field coil. The following table summarizes, as an exemplary embodiment, the maximum current densities for each coil segment. These exemplary values for the current densities are obtained from simulation runs taking into account that different locations of the selection-and-focus field coil require large currents in different coils. Over all, the total of electrical power was at −100 kW. The maximum power in the first inner selection-and-focus field coil was 49 kW, while no more than 38 kW was used for the currents in the second inner selection-and-focus field coil. In each of the outer selection-and-focus field coils no more than 20 kW dissipated.

| | curd [A/m²] | curd [A/mm²] |
|---|---|---|
| 113A | 3.9104E+07 | 39.1042 |
| 113B | 3.0290E+07 | 30.2900 |
| 113C | 1.4279E+07 | 14.2788 |
| 113D | 1.2366E+07 | 12.3658 |
| 115A | 1.4485E+07 | 14.4853 |
| 115B | 1.3682E+07 | 13.6820 |
| 115C | 1.2966E+07 | 12.9664 |
| 115D | 1.2250E+07 | 12.2499 |
| 115E | 1.1529E+07 | 11.5291 |
| 115F | 1.0699E+07 | 10.6994 |
| 115G | 9.9520E+06 | 9.9520 |
| 115H | 8.9570E+06 | 8.9570 |
| 115I | 1.0142E+07 | 10.1418 |
| 115J | 7.8558E+06 | 7.8558 |
| 115K | 4.5355E+06 | 4.5355 |
| 115L | 4.7809E+06 | 4.7809 |
| 117A | 7.0403E+06 | 7.0403 |
| 117B | 7.0148E+06 | 7.0148 |
| 117C | 6.9895E+06 | 6.9895 |
| 117D | 6.9645E+06 | 6.9645 |
| 117E | 6.9398E+06 | 6.9398 |
| 117F | 6.9153E+06 | 6.9153 |
| 117G | 6.8911E+06 | 6.8911 |
| 117H | 6.8671E+06 | 6.8671 |
| 117I | 6.8434E+06 | 6.8434 |
| 117J | 6.8199E+06 | 6.8199 |

Preferably, the coil segments are arranged such that in the direction of the associated coil axis in the obtained current density increases with decreasing distance from the examination area. Various embodiments accessed are to obtain this. Preferred embodiments include that one or more coil segments of the coil arranged closer to the examination area are, compared to one or more coil segments of the same coil arranged further away from the examination area, made of a different material, have thicker windings, are more compact and/or have a higher thickness in the direction of the associated coil axis. For instance, the ratios of the current densities of the different coil segments are used to determine how the wire cross sections should be varied within each coil. In practice, however, deviations from the theoretical values are certainly required since manufacturers of wires generally provide only a limited number of cross section values.

It can further be observed from FIGS. 9 and 10 that in this preferred embodiment a cross section perpendicular to the inner coil axis 115a through a head portion 312h of the second inner pole shoe segment 312 facing the examination area, i.e. a cross section along line X shown in FIG. 10, covers a smaller area than the parallel cross section through a tail portion 312t of said second inner pole shoe segment 312 facing away from said examination area, i.e. along line Y shown in FIG. 10.

Preferably, the outer diameter of said head portion 312h of the second inner pole shoe segment 312 decreases in the direction of the inner coil axis 315a with decreasing distance from the examination area 230. In other words, the outer edges of the head portion 312h are inclined in the direction of the inner coil axis 315a.

Still further, a cross section perpendicular to the inner coil axis 315a through a head portion 313h, 314h of the outer pole shoe segments 313, 314 (the same holds for the other outer pole shoe segments not explicitly shown in FIG. 10) facing said examination area, i.e. along line X, covers a larger area than a parallel cross section through the tail portion 313t, 314t of said outer pole shoe segments 313, 314 facing away from the examination area, i.e. a cross section along line Y.

Still further, the distance of the inner diameter of said head portions 313h, 314h of the outer pole shoe segments 313, 314 (the same holds for the other, not shown outer pole shoe segments) from the inner coil axis 315a decreases in the direction of the inner coil axis 115a with decreasing distance from the examination area 330. In other words, the inner edges of the head portions 313h, 314h are inclined in the direction of the inner coil axis 115a.

As shown, the second inner selection-and-focus field coil 113 and the outer selection-and-focus field coils 116, 117 (the same holds for the other not shown outer selection-and-focus field coils) are moved around the respective pole shoe segment assembling the same outer shape than the corresponding pole shoe segment, which is, however, not necessarily required.

These measures provide for the highest flux density on the surface of the inner pole shoe segments 311, 312 and the inner selection-and-focus field coils 113, 115 facing the examination area, particularly to obtain a high gradient of the magnetic field. It shall be noted, that also the outer edges of the outer pole shoe segments can be inclined into the direction of the inner coil axis 115a to further increase this effect.

For moving the field of view 28 through the examination area, which is conventionally achieved by use of the magnetic focus field, it is generally not required to provide all selection-and-focus field coils with currents. In particular, for moving the field of view 28 in the upper or lower direction, i.e. along the inner direction of the inner coil axis 115a, mainly the two inner selection-and-focus field coils 115, 113 are used. For instance, if a movement of the field of view 28 is desired from the upper selection-and-focus field coil sub-unit 410 in the direction of the lower selection-and-focus field coil sub-unit 420 a current provided to the first inner selection-and-focus field coil of the lower selection-and-focus field coil sub-unit 420 and to the current provided to the second inner selection-and-focus field coil of the upper selection-and-focus field coil sub-unit 410 are increased. Alternatively or in addition the current provided to the first inner selection-and-focus field coil of the upper selection-and-focus field coil sub-unit 410 and the current provided to the second inner selection-and-focus field coil of the lower selection-and-focus field coil sub-unit 420 are decreased. The outer selection-and-focus field coils need not necessarily be used for such a movement.

If a movement of the field of view 28 is desired in a direction perpendicular to the inner coil axis 115a, the outer selection-and-focus field coils are additionally provided with currents. In particular, by said outer selection-and-focus field coils an additional magnetic field is generated in a direction along the desired direction of movement and perpendicular to the inner coil axis 115a. For instance, if a movement from left to right is desired in FIG. 9A a magnetic field is additionally generated having a north pole on the left side and a south pole on the right side (or vice versa). By the amplitude of the current provided to the outer selection-and-focus field coils it can than be controlled how far the field of view 28 shall be moved in this direction.

The above explanation only provides a brief general idea how movement of the field of view can generally be achieved. In practice, of course, the currents need to be controlled precisely which is, however, only a matter of implementation which strongly depends on the exact layout of the overall arrangement.

With respect to the pole shoes it shall be noted that they are preferably made from magnetically conductive sheets, wherein sheets forming the inner pole shoe segments 311, 312 and an adjacent head portion 317h of the pole shoe yoke 317 of the pole shoe 310 (the same holds for the inner pole shoe segments and the pole shoe yoke of the other pole shoe 320) are arranged along a direction parallel to the inner coil axis 315a. Sheets forming the tail portion 317t of the pole shoe yoke 317 (the same holds for the other pole shoe yoke 327) are preferably arranged in a direction substantially perpendicular to the inner coil axis 315a. This provides for an optimum connectivity of the magnetic flux.

In case of using two or more pole shoes that are connected by a pole shoe bearing 330, as shown in FIG. 8, it is preferred that also the pole shoe bearing 330 is made from magnetically conductive sheets that are arranged adjacent to each other in the same direction as sheets forming the portion of the pole shoe to which the pole shoe bearing is connected. For instance, if the pole shoe bearing connects to the head portions of the pole shoe yokes, the sheets of the pole shoe bearing are preferably arranged in a direction perpendicular to the inner coil axis. The sheets forming the pole shoe bearing are also arranged in a direction perpendicular to the inner coil axis 315a at least at the connection to the pole shoe yokes. Generally, the sheets should be arranged such that the best magnetic flux connectivity is achieved.

Figure 11:
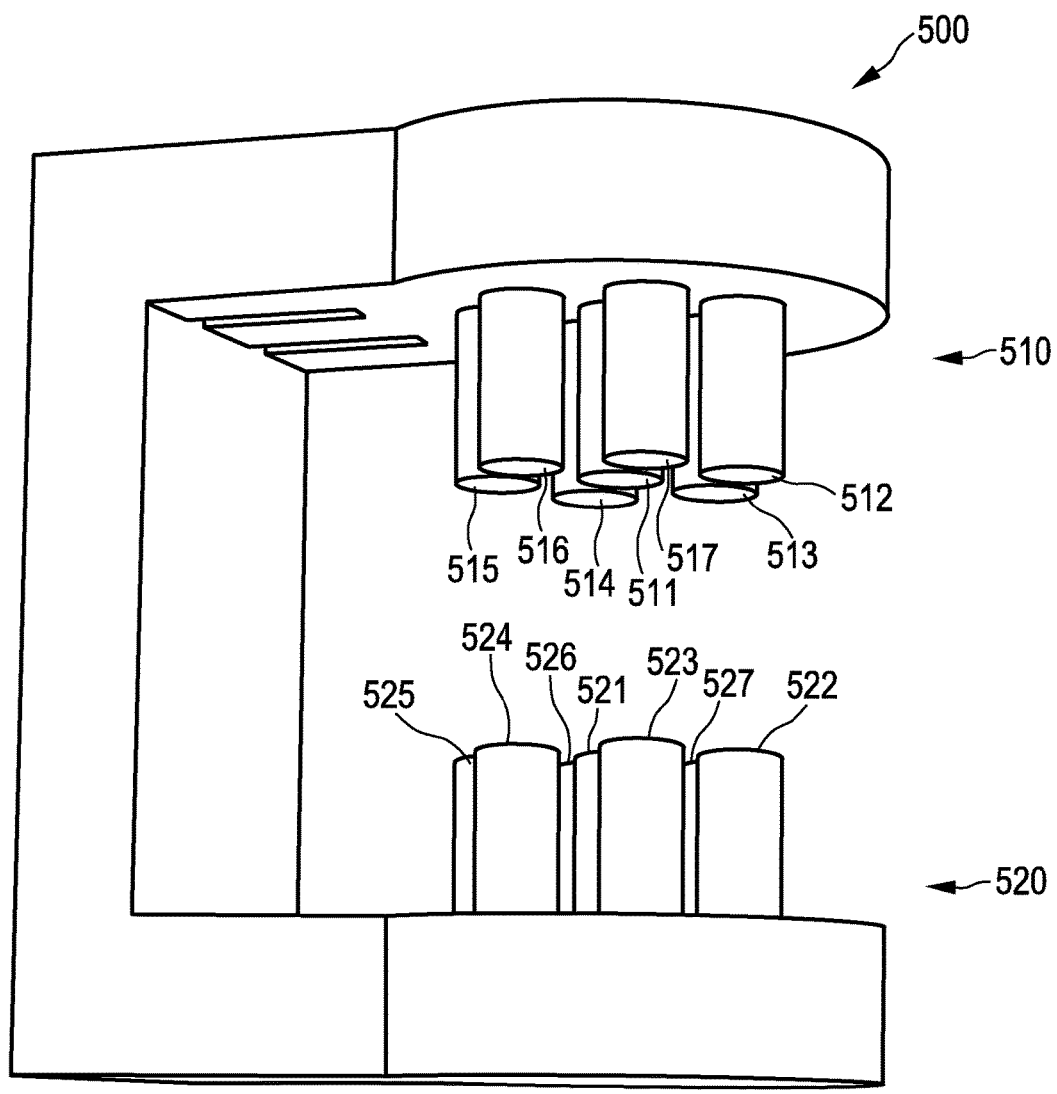
FIG. 11 shows a perspective view of another embodiment of a pole shoe arrangement according to the present invention.

FIG. 11 shows a perspective view of an embodiment of a pole shoe arrangement 500 according to the present invention. Compared to the pole shoe arrangement 300 shown in FIG. 8, the outer pole shoe segments are not formed in this embodiment as ring-shaped segments, but the outer pole shoe segments 512-517 (of the first pole shoe 510) and 522-527 (of the second pole shoe 520) are formed as bar-shaped cylinders, preferably in the same shape as the inner pole shoe segments 511, 521. The advantages of such an arrangement are primarily cost savings since only one or two kinds of pole shoes need to be manufactured. The main advantage is realized, if at least a second ring of pole shoes (not shown in FIG. 11) is arranged around the central pole shoe. In other embodiments, also further forms of the pole shoe segments, in particular of the outer pole shoe segments, are useable.

Figure 12:
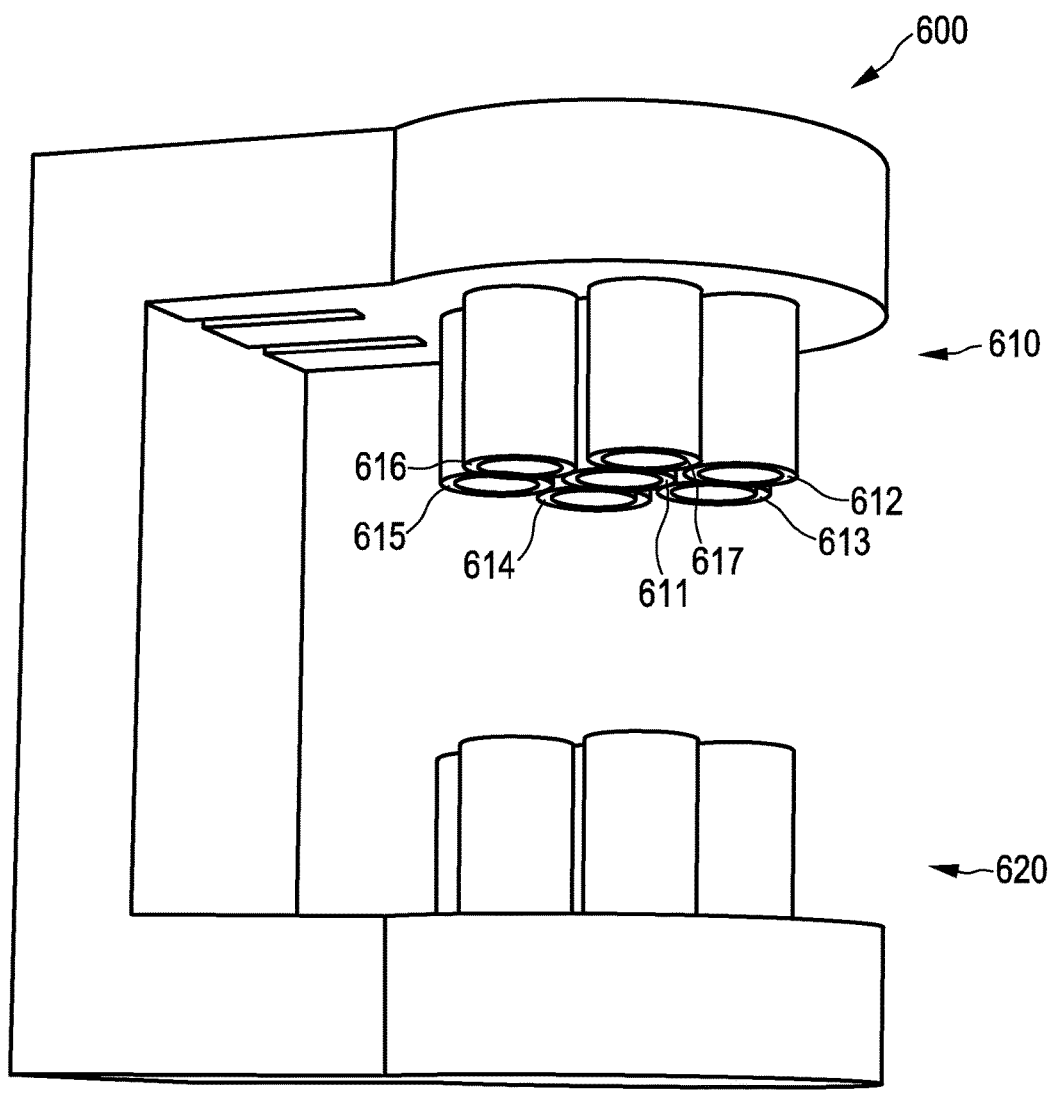
FIG. 12 shows a perspective view of another embodiment of a selection-and-focus field coil arrangement according to the present invention.

FIG. 12 shows a perspective view of another embodiment of a selection-and-focus field coil arrangement 600 according to the present invention. In this embodiment the pole shoe arrangement 500 depicted in FIG. 11 is used, wherein each pole shoe segment is provided with an individual selection-and-focus field coil wound around a ring-shaped coil 611-617 (for the upper selection-and-focus field coil sub-unit 610; the same holds for the lower selection-and-focus field coil sub-unit 620).

Figure 13:
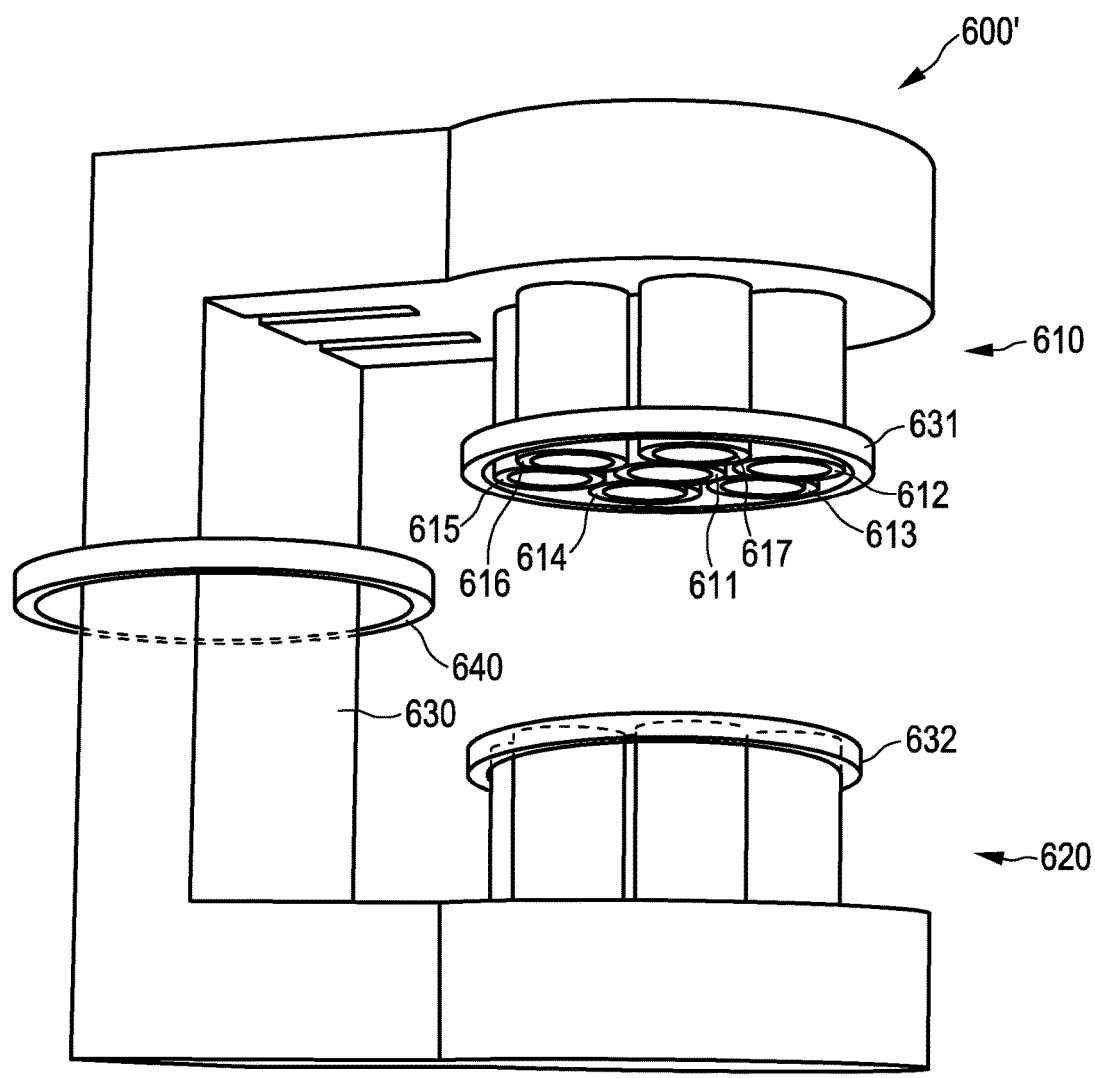
FIG. 13 shows a perspective view of still another embodiment of a selection-and-focus field coil arrangement according to the present invention.

There are further embodiments of selection-and-focus field coil arrangements. For instance, in still another embodiment of a selection-and-focus field coil arrangement 600' according to the present invention shown in FIG. 13 a large cylindrical magnetic field coil 631, 632 is placed outside of and around each selection-and-focus field coil sub-unit 610, 620. Further, it is possible to arrange one or more additional magnetic field coil(s) 640 around the magnetic bearing 630 to further strengthen the magnetic field.

It shall be noted that in addition to the various selection-and-focus field coils additionally a permanent material in each selection-and-focus field coil sub-unit may be provided to further strengthen the generation of the magnetic selection field for generating the selection-and-focus field coil. This permanent magnet would preferably be located close to the examination zone substituting parts of the soft-magnetic material.

Further, it shall be noted that the cooling means are preferably provided for cooling some or all of the coils. The cooling means may use a cooling fluid like water or oil. The coils may be made from copper or aluminum, but it is also possible to make them from superconductive material, which would then be cooled by use of an appropriate cooling material such as helium. In case of high temperature superconductive conductors the cooling can be achieved by use of gaseous helium. In case of low temperature superconductive conductors the cooling can be achieved by use of liquid helium.

Using the geometry described above different simulation runs were performed. The results obtained this way are summarized in the following.

Figure 14:
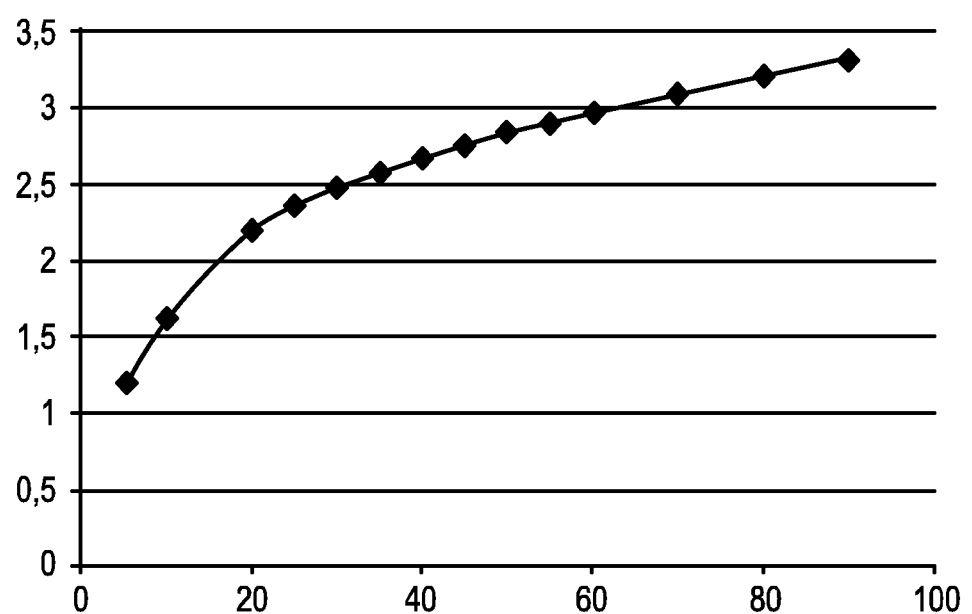
FIG. 14 shows a diagram showing the gradient field strength as a function of electrical power for an MPI apparatus according to the present invention.

For the FFP located at the center of the geometry a gradient field strength of 2.5 T/m was obtained with an electrical power of 30 kW. Using 90 kW of electrical power the gradient field strength increased to 3.3 T/m. FIG. 14 shows how the gradient field strength increases with the electrical power. For these simulations only the inner selection-and-focus field coils. No current flew in the outer selection-and-focus field coils. In particular, the electrical power in the second inner selection-and-focus field coils was four times larger than in the first inner selection-and-focus field coils.

With respect to movement in z-direction, using the inner selection-and-focus field coils the FFP could be placed on the z-axis at a distance of 10 cm from the origin. With a total power consumption of 92 kW the gradient field strength obtained was 2.5 T/m. The electrical power was distributed among the coils as follows. For the pole shoe in the direction in which the FFP was moved the first inner selection-and-focus field coil dissipated 49 kW, while no current flew in the second inner selection-and-focus field coil. For the pole shoe in the other direction the first inner selection-and-focus field coil dissipated 5 kW, while 38 kW were necessary in the second inner selection-and-focus field coil.

With respect to movement in x- and/or y-direction, using the outer selection-and-focus field coils the FFP can be moved along x and/or y. For instance, in one of the simulations, the FFP was placed on the x-axis at a distance of 10.1 cm from the origin. Here a total electrical power of 100 kW was used. A power of 40 kW dissipated in four of the outer selection-and-focus field coil, while the remaining 60 kW were used in the inner selection-and-focus field coils. The gradient field strength obtained was 2.2 T/m. Nevertheless, the gradient was rather inhomogeneous. Using common computation methods the values obtained are $G_x=-0.69$ T/m and $G_y=-1.51$ T/m.

For certain applications (MR) it is desirable to generate a magnetic field which does not have an FFP but is rather homogeneous. Simulations were therefore performed in which the current direction in one of the inner pole-shoes was reversed. Using all coils and different distributions of the available power (100 kW) the maximum observed field strength at the origin was 0.45 T. The field strength increases along z and decreases along x/y.

To compute the energy stored in the magnetic field the integral $$E = \frac{1}{2} \int_V B \cdot H \, dV$$

is evaluated over volume V. Within our simulations the maximum observed energy stored in the magnetic field was below 40 kJ. The maximum was seen in a simulation trying to obtain a homogeneous (MR) field.

The specific absorption rate (SAR) is a measure to quantify the imported heat into the (human) body during a medical examination. There are certain limits and guidelines, which typically include short-term and long-term limits, as well as partial body and whole body limits. Peripheral nerve stimulation (PNS) is an effect in which the nerves and muscles inside the (human) body are stimulated by induced electric field within the human body. The electric field is the consequence of the change of the magnetic field, therefore it is proportional to magnetic field strength and its derivate with time (generally dB/dt, for sinusoidal excitation in Fourier-space: $\omega B$).

In MPI scanners for small-size objects, SAR and PNS did not yet present a limit, as the object (e.g. a small animal) is small. The present invention provides a solution for building a human-size scanner. Here, SAR and PNS might become potentially limiting factors.

In known MPI scanners the current of the magnetic drive field was kept constant during the examination, independent of the position of the field-free point. This cannot be continued in human-size scanners for reasons of SAR and PNS. In fact, the current was chosen such that (e.g.) 20 mT peak amplitude was generated in the very center of the examination area (generally forming a bore). Due to the non-homogeneity of the magnetic field, this meant that higher magnetic drive field amplitudes were generated at other positions.

Figure 15A:
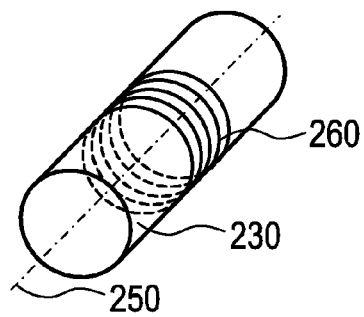
FIG. 15 shows an embodiment of drive field coils.
Figure 15B:
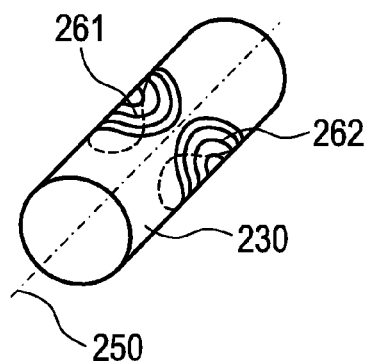

FIGS. 15A and 15B show the coils employed to generate the magnetic drive field around the examination area 230, in which the patient is placed. For a field along the axis 250, a solenoid 260 (FIG. 15A) is used, for the two orthogonal axes saddles coils 261, 262 (FIG. 15B) are used. It shall be noted that generally there is another (not shown) pair of saddle coils orthogonal to the saddle coils 261, 262.

Figure 16:
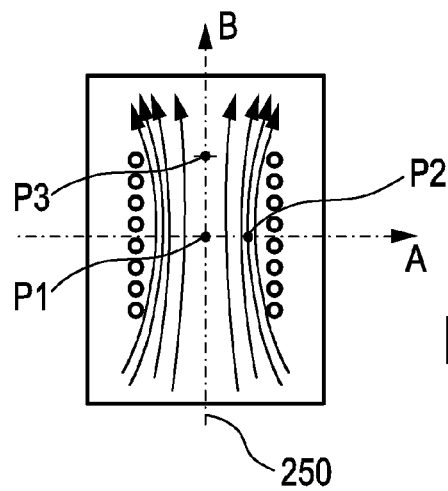
FIG. 16 shows the magnetic field in a solenoid coil.

FIG. 16 shows the magnetic field lines within the bore of a solenoid coil 260. Based on this coil type, the following argumentation will be outlined. The argumentation for saddle coils would generally be identical.

In FIG. 16, three points are labelled: P1, P2, and P3. In the middle of the bore, the point P1 shall see 20 mTpk/$\mu_0$ of drive field. In known MPI scanners the current through the solenoid coil 260 is chosen such as to achieve these 20 mTpk/$\mu_0$ at the center point P1. This current is kept identical throughout the whole experiment, independent of the location of the FOV.

Figure 17A:
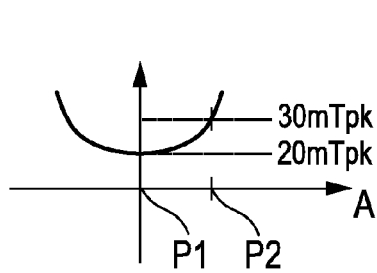
FIG. 17 shows the field strengths along two orthogonal axes.
Figure 17A:
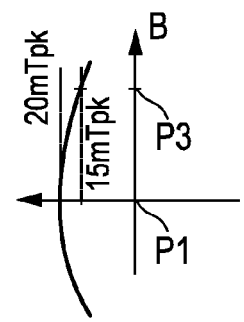

Within human-size scanners, the field of view gets enlarged by additional focus field movements. The focus field brings the center of the field of view (i.e. the volume that is sampled by the fast movement of the field-free point by means of the drive field) to any desired place within the bore. For example, the field of view is shifted to position P3. If the current is kept constant this position P3 will see a field strength of only 15 mTpk/$\mu_0$ (as shown in FIG. 17B). So the image quality/resolution/particle response at this location is deteriorated. On the other hand, if the field of view is shifted (by means of the focus field) to position P2, then the field strength at this location will be higher, e.g. 30 mT (as shown in FIG. 17A). The disadvantage is now essentially that there is a higher drive field amplitude than required for the imaging process. In fact, the image would not improve any further, but essentially unnecessary power is fed into the patient's body, i.e. SAR. Also, if PNS applies, the phenomenon will be more severe.

The first requirement for a suitable solution for human size scanners comes from the point P3. Here, it is required that also at this point with weak sensitivity (i.e. generated field strength divided by current flow in the coil) the field strength shall be 20 mTpk/$\mu_0$ as is required for proper imaging quality. These 20 mTpk/$\mu_0$ can only be achieved by increased current.

Now it would be an unnecessary situation if this higher current is kept constant for the whole experiment, i.e. for all positions that shall be scanned. Hence, the proposed solution is to reduce the current once the sensitivity of a given point is higher. Particularly, P2 will require a "normal" current, whilst P3 will require a further reduced current.

Overall, this rule for the current is beneficial in several aspects, i.e. provides a reduction of SAR, a reduction of PNS and a reduction of dissipated average power in the coils (this translates directly to cost savings in the hardware).

In a further embodiment the current provided to one or more drive field coils is adapted as a function of the location of the FFP (or field of view). In order to generate, e.g. 20 mT peak amplitude, at a location, the current is chosen as a function of the sensitivity (in terms of (Ampere/Meter) per Ampere) of the coil at this location. Provided the gradient of the selection-and-focus field is homogenous (i.e. independent of the location), this rule generates a deflection (distance of movement of the FFP under drive-field influence) that would also be homogeneous (i.e. independent of the location).

Furthermore, since the selection-and-focus field is not homogeneous in reality, this shall also be considered in the rule for choosing the drive-field current. By this means, e.g. a constant-volume field of view can be generated that is not be distorted by in-homogeneities of the selection-and-focus field.

According to another embodiment the pairs of saddle coils (one pair being shown in FIG. 15B) are split (rather than three coils surrounding the object of examination) to provide a reduction of SAR, a reduction of PNS and a reduction of dissipated average power in the coils (this translates directly to cost savings in the hardware).

In the known MPI scanner the two saddle coils 261, 262 make up one pair which is electrically connected in series, i.e. both saddle coils 261, 262 have identical currents that flow through them. According to an improvement proposed here the saddle coils 261, 262 are split and are provided with independent and, typically, non-identical currents. The benefits are that, despite double power-generating and power-filtering hardware is needed, all components have only half the current, i.e. they can be realised as smaller components, keeping cost nearly unaffected. Further, the two saddle coils may simultaneously be used as two separate receive coils. Together with another receiver, the two receivers constitute two independent measures, which are influenced by independent thermal noise (body noise, coil noise, receiver noise). By proper reconstruction, this is an additional benefit for the system signal-to-noise ratio, hence improving image quality.

Figure 18:
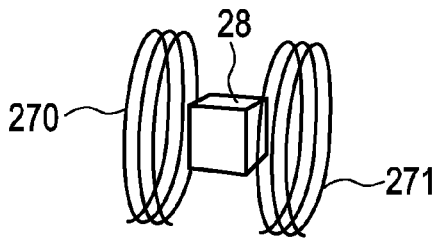
FIG. 18 shows two coplanar drive field coils for explanation of another embodiment.

For the sake of simplicity, a Helmholtz-like structure as shown in FIG. 18 of two flat coils 270, 271 shall be regarded (instead of the more complicated saddle coils as shown in FIG. 15B). If the FFP is in the middle, both coils 270, 271 have identical sensitivities towards this point, as is shown at point P1 in FIG. 19B. In order to minimise induced magnetic field, both coils 270, 271 shall contribute equally to field-generation, so have the same current. Then the magnetic field, contributing both to SAR and PNS, is induced equally near to both coils 270, 271.

Figure 19A:
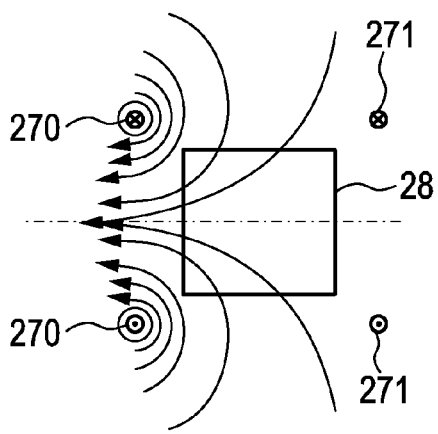
FIG. 19 shows the magnetic fields generated by the coplanar coils shown in FIG. 18 when provided with different coil currents.
Figure 19B:
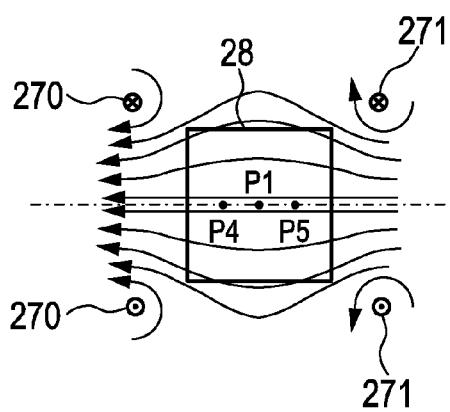

If the FFP is not in the middle (e.g. point P4 in FIG. 19B), then the coil 270 (i.e. the coil that is nearer to the FFP) will have a better sensitivity than the other coil 271. For the same reasons as above, it will generally be advantageous to have the nearer coil generate more of the magnetic drive field (provided all body parts are of identical sensitivity in a medical sense). For comparison, FIG. 19B shows the magnetic field if only the coil 270 is provided with current.

Figure 20A:
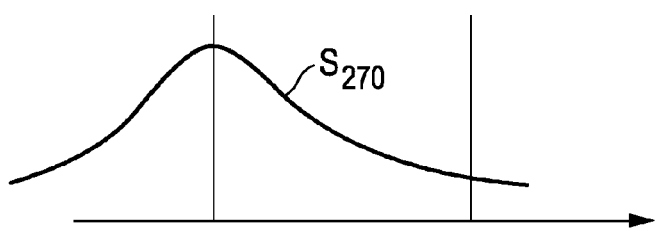
FIG. 20 shows the coil sensitivities for the coplanar coils shown in FIG. 18.
Figure 20B:
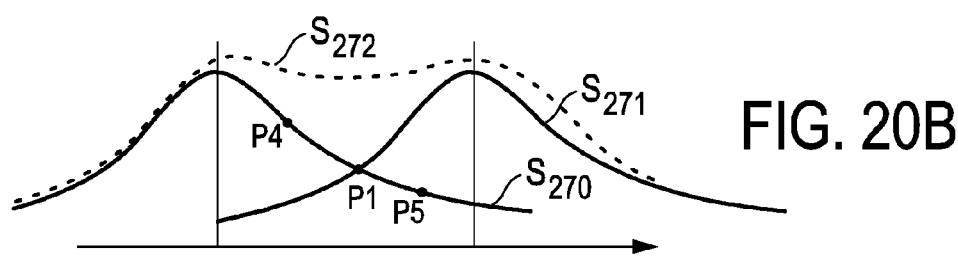

FIG. 20B shows the field generated by identical currents in both coils 270, 271, which is proportional to the respective sensitivities $S_{270}$, $S_{271}$ (in terms of magnetic field strength per generating current; the cumulative sensitivity is indicated by $S_{272}$). For instance, at position P4, the sensitivity $S_{270}$ from the coil 270 is higher than the sensitivity $S_{271}$ from the coil 271. Therefore, the coil 270 shall contribute more in order to minimise SAR, PNS, and power losses in the coils. However, for reasons of continuity, it will not be a "winner takes all" current distribution, but a smooth transition between the coils. So at position P4 it will not be the case that the coil 270 has all the current and the coil 271 will be switched off as shown in FIG. 20A.

Preferably, an algorithm will consider both SAR and PNS, and both on a "global" scale and a local scale. Therefore, it will typically be beneficial to have all available field generators participate in order to minimise the excess field near to the conductors.

If one part of the body of the patient is more sensitive to magnetic fields than another, the current can be distributed such as to favour the less sensitive part of the body.

Figure 21:
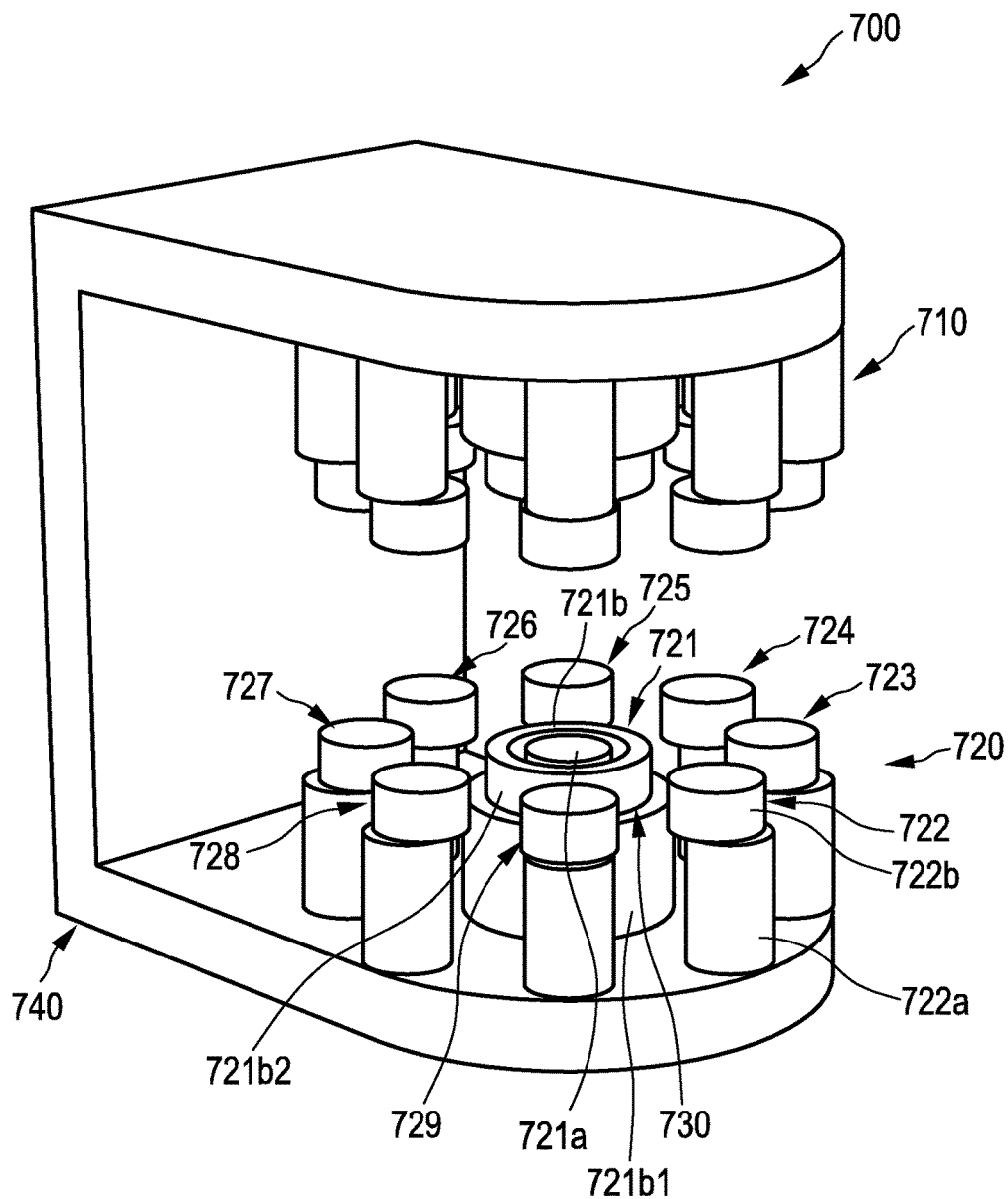
FIG. 21 shows a perspective view of another embodiment of a pole shoe arrangement according to the present invention.
Figure 22:
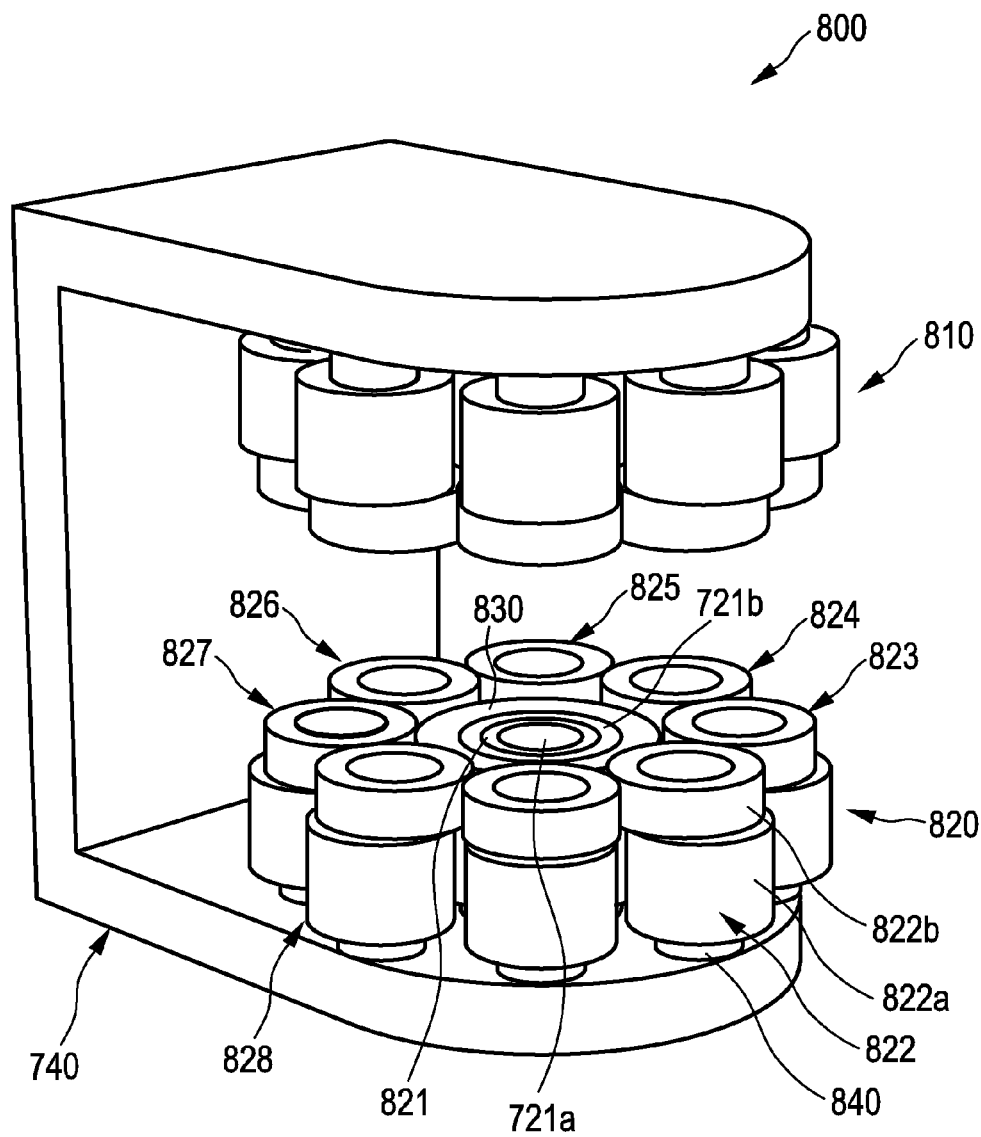
FIG. 22 shows a perspective view of another embodiment of a selection-and-focus field coil arrangement according to the present invention using the pole shoe arrangement shown in FIG. 21.

FIG. 21 shows a perspective view of another embodiment of a pole shoe arrangement 700 according to the present invention, and FIG. 22 shows a perspective view of a corresponding embodiment of a selection-and-focus field coil arrangement 800 according to the present invention using the pole shoe arrangement 700 shown in FIG. 21. In this embodiment each pole shoe 710, 720 comprises a central inner pole shoe segment 721 surrounded by outer pole shoe segments 722-729 (only the pole shoe segments for the lower pole shoe 720 are explicitly indicated in FIG. 21 and explained below; the upper pole shoe 710 is preferably designed in the same manner). In this exemplary embodiment eight outer pole shoe segments are provided, but different numbers of outer pole shoe segments are also possible. The selection-and-focus field coil arrangement 800 comprises an upper selection-and-focus field coil sub-unit 810 and a lower selection-and-focus field coil sub-unit 820 each comprising a number of coils 821-830 (again, only the coils for the lower selection-and-focus field coil sub-unit 820 are explicitly indicated in FIG. 22 and explained below; the upper selection-and-focus field coil sub-unit 810 is preferably designed in the same manner).

In this embodiment the inner pole shoe segment 721 comprises an inner cylinder 721a made of soft-magnetic material surrounded by a coil 821 shaped like a tube. The inner cylinder 721a of the inner pole shoe segment 721 is surrounded by a ring 721b of soft-magnetic material which by itself is surrounded by another coil 830. The ring 721b of soft-magnetic material has one (or more) step(s) 730 as shown in FIG. 21, i.e. the outer diameter in the lower section 721b1 of the ring 721b facing away from the opposing of the pole shoe 710 is larger than the outer diameter in the upper section 721b2 of the ring 721b facing the opposing of the pole shoe 710. Alternatively, the steps are realized as a bezel.

Preferably, the step also exists in the outer diameter of the coil 830, i.e. this coil preferably has a constant thickness, so that the outer diameter in the lower section of the coil 830 is larger than in the upper section of the coil 830.

Each coil 821, 830 preferably covers its associated pole shoe segment 721, 721b entirely, i.e. it reaches from the connection to the C-arm structure 740 (i.e. the pole show bearing) to the tip of the pole-shoe segment. Alternatively, each coil does not need to be connected to the C-arm structure 740 such that some space remains. The advantages of the space 840 are that it can be used for mounting devices and feeding equipment and that the coils can be manufactured more easily.

Further, each coil 821, 830 preferably comprises different coil segments connected in series. Each segment has a specific winding such that the current densities vary along the pole-shoes. The modifications of the coils explained above with respect to other figures can thus be used here as well.

In this embodiment the outer pole shoe segments 722-729 each comprises a lower part 722a and an upper part 722b connected to each other (indicated by reference signs only for the outer pole shoe segment 722), where the lower part 722a is connected to the C-arm structure 740. Both the upper and lower parts 722a, 722b are surrounded by coils 822a, 822b connected in series. The upper parts 722b are shifted towards the inner pole shoe segment 721 relative to the lower parts 722a and preferably have a larger diameter than the lower parts 722a. This shifting is possible since, due to the step 730 on the inner pole shoe segment 721, the required space is available.

Each coil 822-829 can cover the entire respective pole shoe segment 722-729, i.e. it can reach from the connection to the C-arm structure 740 to the tip of the respective pole shoe segment 722-729. Alternatively, each coil 822-829 does not need to be connected to the C-arm structure 740 such that some space 840 remains as shown in FIG. 22.

In a preferred embodiment each coil 822-829 comprises different segments connected in series. Each segment has a different winding such that the current densities vary along the pole shoe segment.

The inner pole shoe segment 721 together with its associated coils 821, 830 primarily generates a magnetic field with a FFP. A variation of the currents in the coils 821, 830 allows movement of the FFP along the vertical axis. The outer pole shoe segments 722-729 together with their associated coils 822-829 primarily allow movement of the FFP in the directions of the horizontal axes.

In the embodiments discussed above and in the following, pole shoe segments usually have cylindrical shapes with circular base areas. Other shapes can also be realized. For instance, cylinders with ellipses as base area can be useful in other embodiments.

The upper and lower pole shoes do not necessarily have to be connected via a C-arm structure. The connection can also be realized by use of other carrier structures, e.g. by use of, for instance, four bars made of soft-magnetic material, one at each corner.

Figure 23:
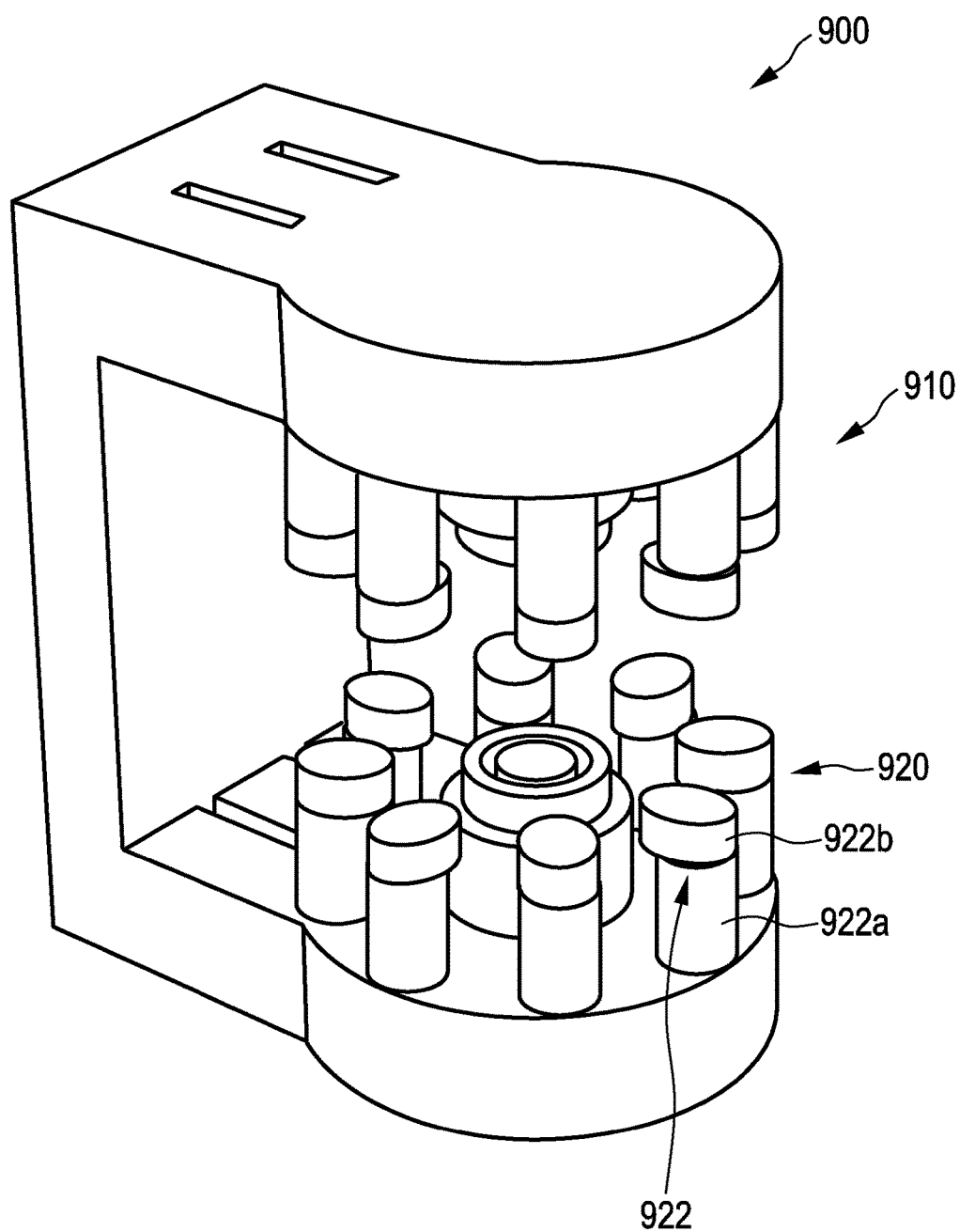
FIG. 23 shows a perspective view of another embodiment of a pole shoe arrangement according to the present invention.

FIG. 23 shows another embodiment of a pole shoe arrangement 900, in which the upper parts 922b of the outer pole shoe segments 922 have an elliptical cross section (this, preferably, holds for all outer pole shoe segments of both pole shoes 910, 920), whereas the lower parts 922a have a circular or an elliptical cross section. This deviation from the circular shape allows a better utilization of the available space. Certainly, other cross sections like rectangular or rectangular-like cross sections are generally also possible.

Figure 24:
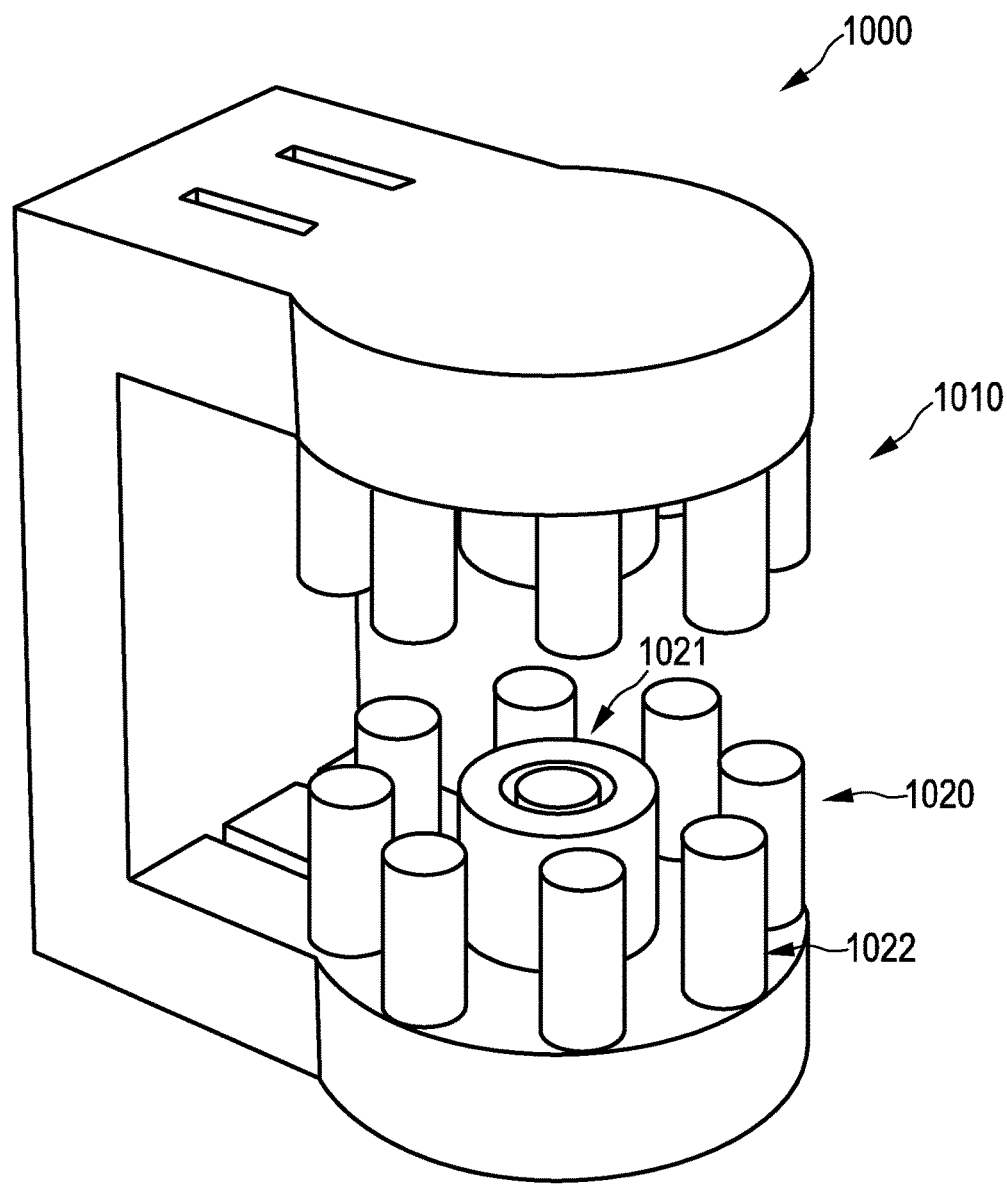
FIG. 24 shows a perspective view of another embodiment of a pole shoe arrangement according to the present invention.

FIG. 24 shows another embodiment of a pole shoe arrangement 1000, in which the pole shoe segments have the simplest possible shape. There is no step at the inner pole shoe segment 1021 and the outer pole shoe segments 1022 are not separated into lower and upper parts. This preferably holds for both pole shoes 1010, 1020. The advantage of such an implementation is a minimization of manufacturing costs. Alternatively, the implementation of FIG. 24 can also be realized with a step on the inner pole shoe segment as shown in FIGS. 21 and 23.

Figure 25:
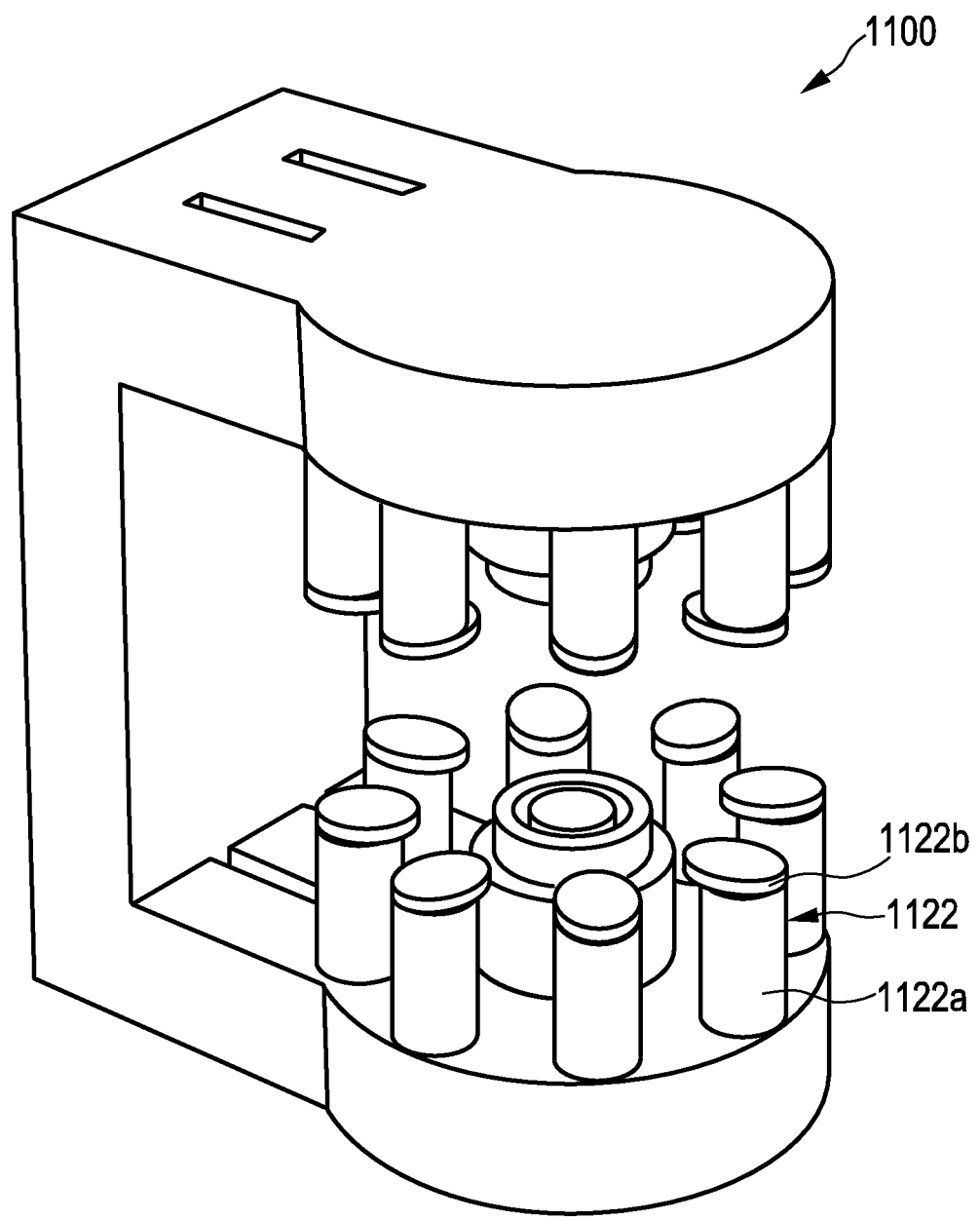
FIG. 25 shows a perspective view of another embodiment of a pole shoe arrangement according to the present invention.
Figure 26:
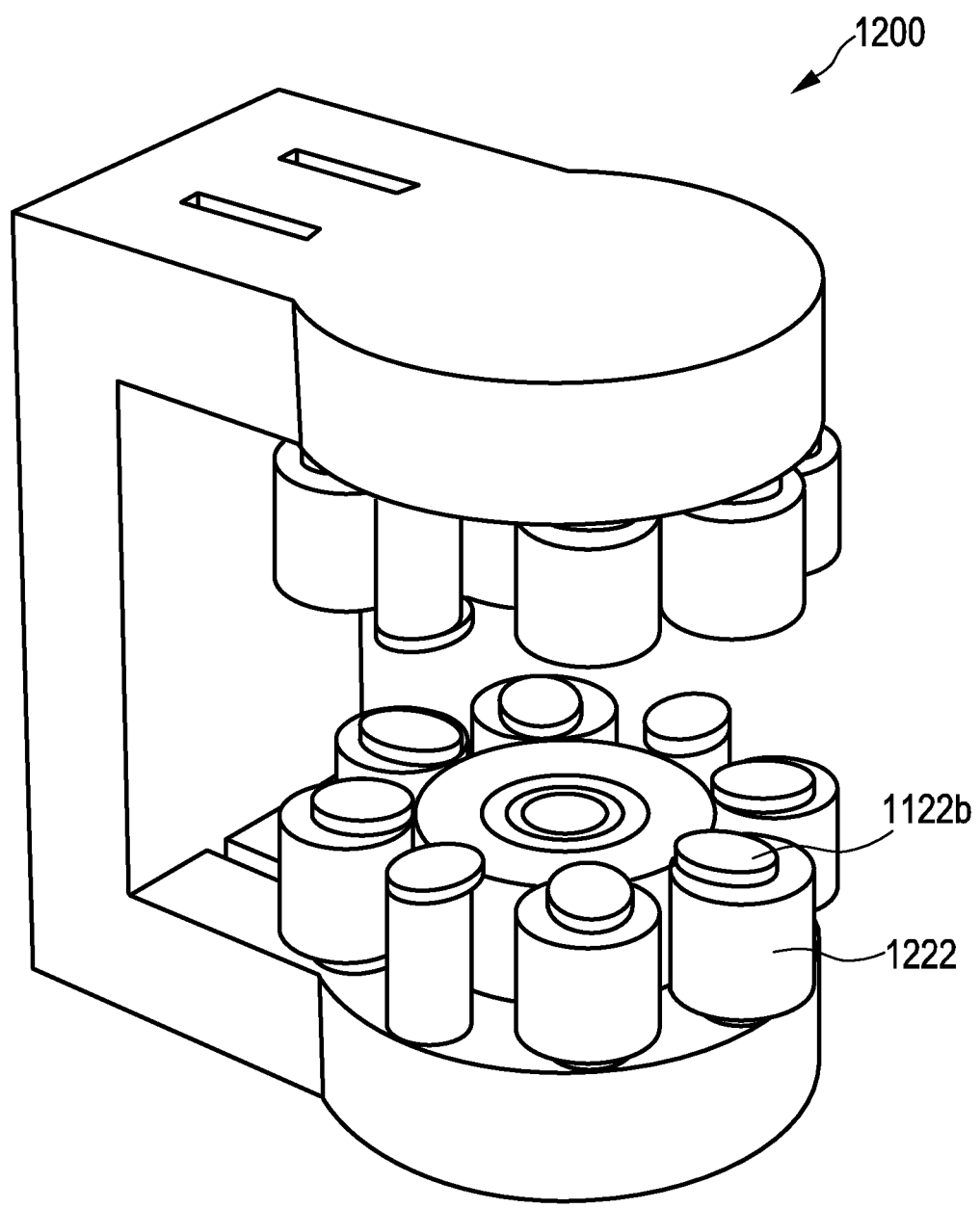
FIG. 26 shows a perspective view of another embodiment of a selection-and-focus field coil arrangement according to the present invention using the pole shoe arrangement shown in FIG. 25.

FIG. 25 shows a perspective view of another embodiment of a pole shoe arrangement 1100 according to the present invention, and FIG. 26 shows a perspective view of a corresponding embodiment of a selection-and-focus field coil arrangement 1200 according to the present invention using the pole shoe arrangement 1100 shown in FIG. 25. In this embodiment the outer pole shoe segments 1122 each comprise a small upper part 1122b (like a hat) made of soft-magnetic material meant to guide the magnetic field. These "hats" 1122b preferably have an elliptical cross section, but are not surrounded by electromagnetic coils as can be seen in FIG. 26. Only the lower part 1122a (preferably having a circular cross section) of the outer pole shoe segments 1122 is surrounded by a coil 1222. This embodiment is an alternative with reasonable magnetic field characteristics at reasonable costs. The inner pole shoe segment and the associated coils are preferably configured as in the embodiment shown in FIG. 22 or 24.

Figure 27:
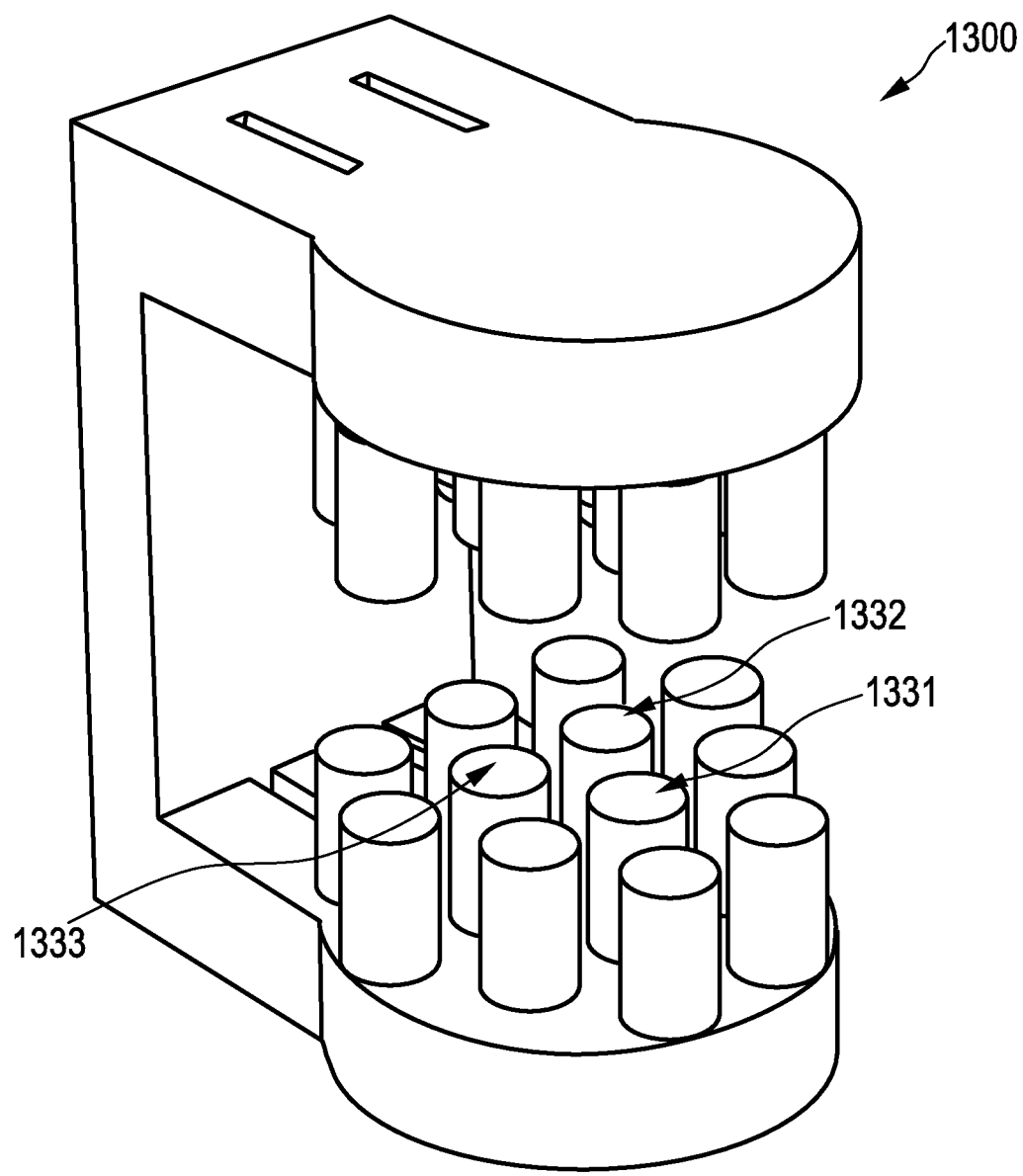
FIG. 27 shows a perspective view of another embodiment of a pole shoe arrangement according to the present invention.
Figure 28:
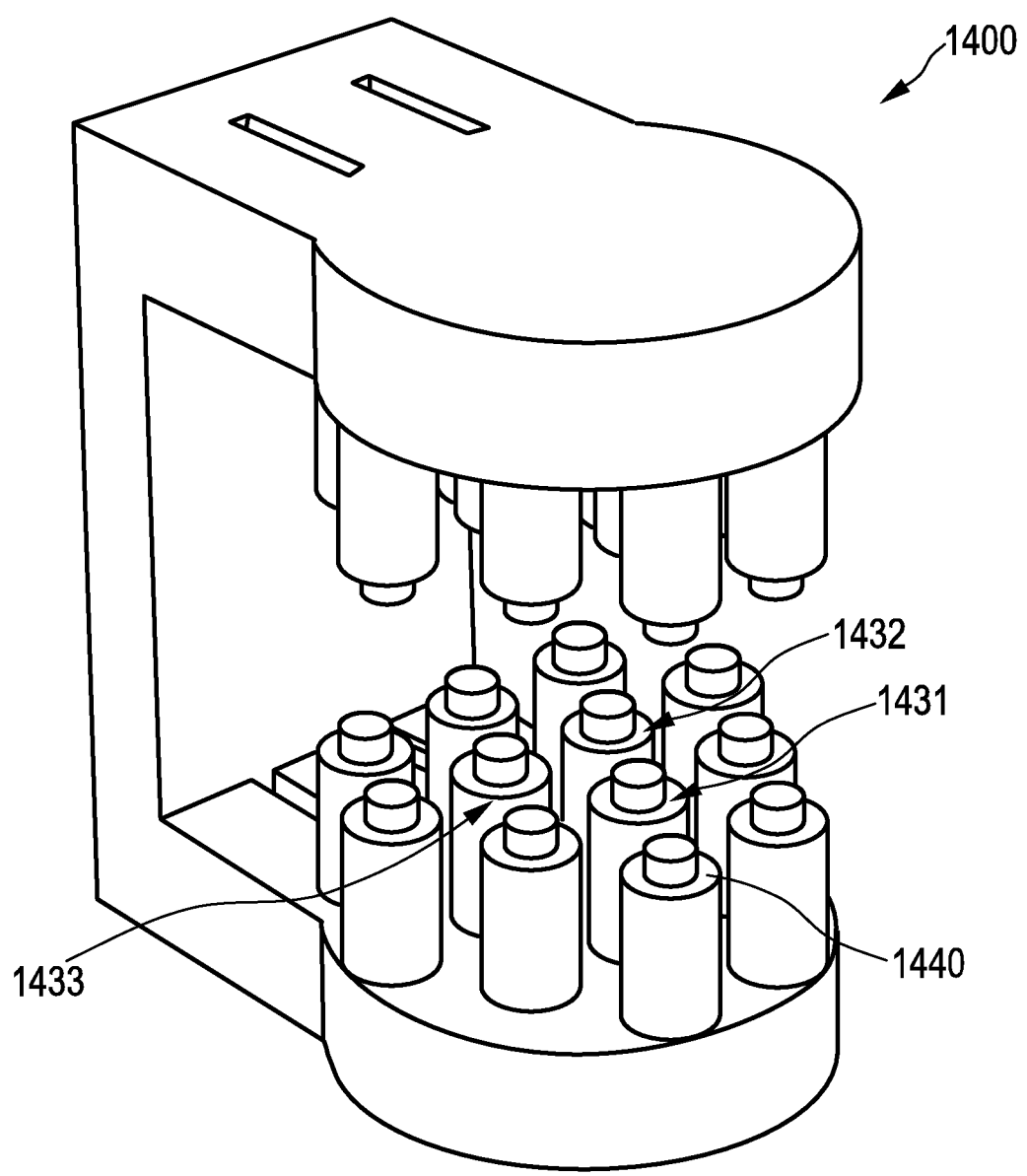
FIG. 28 shows a perspective view of another embodiment of a pole shoe arrangement according to the present invention.

FIGS. 27 and 28 show embodiments of pole shoe arrangement 1300 and 1400, in which the single inner pole shoe segment is exchanged by three inner pole shoe segments 1331, 1332, 1333 (in FIG. 27) and 1431, 1432, 1433 (in FIG. 28) mounted at the corners of a triangle. In the pole shoe arrangement 1300 shown in FIG. 27 the pole shoe segments are cylinders with a constant outer diameter whereas in the pole shoe arrangement 1400 shown in FIG. 28 the pole shoe segments are cylinders having steps 1440 at their tips. As an alternative to these steps, pole shoe segments with a bezel are also possible.

Figure 29:
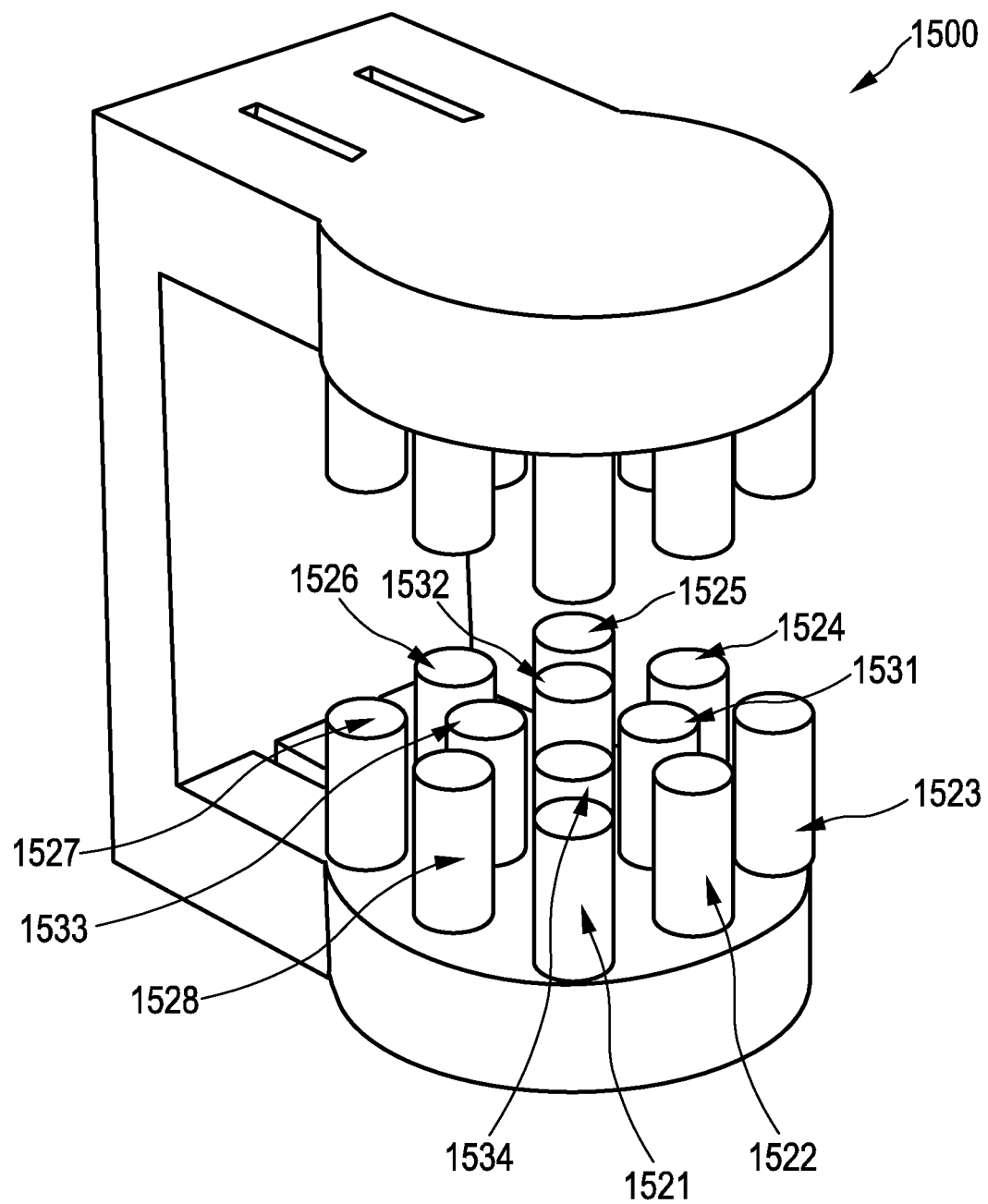
FIG. 29 shows a perspective view of another embodiment of a pole shoe arrangement according to the present invention.

FIG. 29 shows still another embodiment of a pole shoe arrangement 1500. Here the single inner pole shoe segment is exchanged by four inner pole shoe segments 1531-1534 mounted at the corners of a square. Similarly, the outer pole shoe segments 1522-1529 are arranged along the edges of an outer square.

In the embodiment shown and explained above, particularly in FIGS. 21 to 29, one ring of outer pole shoe segments surrounds the inner pole shoe segment for each pole shoe. Alternatively, more than one ring of outer pole shoe segments can be provided. Further, equal numbers of pole shoe segments are provided in the upper and lower pole shoes. Alternatively, the number of pole-shoe segments can differ for the two pole shoes. Still further, each pole shoe segment in a pole shoe is arranged opposite to a corresponding pole shoe segment in the other pole shoe. Alternatively, the pole shoe segments of the two pole shoes can be mounted shifted with respect to each other. Still further, it can be advantageous, if the pole shoe segments are not built exactly identical. For instance, choosing a larger height for the outer pole shoe segments provides better features with respect to achievable gradient field strength and movability of the FFP. Also, different diameters can be realized. Finally, the position of the pole shoe segments relative to the C-arm structure could be chosen differently from the arrangement as shown in the figures, e.g. the pole shoe segments could be mounted at positions rotated around an axis parallel to the inner pole shoe segment.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An apparatus for influencing and/or detecting magnetic particles in a field of view, which apparatus comprises:
    selection-and-focus means for generating a magnetic selection-and-focus field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view and for changing the position in space of the field of view within an examination area,
    wherein said selection-and-focus means includes at least one set of selection-and-focus field coils and a selection-and-focus field generator unit for generating selection-and-focus field currents to be provided to said at least one set of selection-and-focus field coils for controlling the generation of said magnetic selection-and-focus field,
    wherein said at least one set of selection-and-focus field coils includes
        at least one inner selection-and-focus field coil being formed as a closed loop about an inner coil axis, and
        a group of at least two outer selection-and-focus field coils arranged at a larger distance from said inner coil axis than said at least one inner selection-and-focus field coil and at different angular positions, each outer selection-and-focus field coils being formed as a closed loop about an associated outer coil axis; and
    drive means including a drive field signal generator unit and drive field coils for changing the position in space and/or size of the two sub-zones in the field of view by means of a magnetic drive field so that the magnetization of the magnetic material changes locally.

2. An apparatus as claimed in claim 1, wherein said at least one set of selection-and-focus field coils includes
    a first inner selection-and-focus field coil, and
    a second inner selection-and-focus field coil being formed as a closed loop ab ut said inner coil axis and having a larger diameter than said first inner selection-and-focus field coil.

3. An apparatus as claimed in claim 1,
    wherein at least one of said at least one inner selection-and-focus field coil and said outer selection-and-focus field coils are split into at least two coil segments,
    wherein coil segments of a coil are arranged adjacent to each other in the direction of the associated coil axis, and
    wherein adjacent coil segments are electrically connected.

4. An apparatus for influencing and/or detecting magnetic particles in a field of view, which apparatus comprises:
    selection-and-focus means for generating a magnetic selection-and-focus field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view and for changing the position in space of the field of view with in an examination area, wherein said selection-and-focus means includes at least one set of selection-and-focus field coils and a selection-and-focus field generator unit for generating selection-and-focus field currents to be provided to said at least one set of selection-and-focus field coils for controlling the generation of said magnetic selection-and-focus field, wherein said at least one set of selection-and-focus field coils includes
at least one inner selection-and-focus field coil being formed as a closed loop about an inner coil axis and
a group of at least two outer selection-and-focus field coils arranged at a larger distance from said inner coil axis than said at least one inner selection-and-focus field coil and at different angular positions, each outer selection-and-focus field coils being formed as a closed loop about an associated outer coil axis;

drive means including a drive field signal generator unit and drive field coils for changing the position in space and/or size of the two sub-zones in the field of view by means of a magnetic drive field so that the magnetization of the magnetic material changes locally; and wherein said drive field coils includes
two pairs of saddle coils arranged around a central symmetry axis perpendicular to said inner coil axis, and
a solenoid coil arranged around said central symmetry axis.

5. An apparatus as claimed in claim 1, wherein said drive field signal generator unit is adapted for at least one of
generating and providing individual drive field currents to one or more of said drive field coils, and
generating drive field currents in dependence on at least one of a sensitivity and a position of at least one of the first sub-zone and the field of view within the examination area.

6. An apparatus for influencing and/or detecting magnetic particles in a field of view, which apparatus comprises:
selection-and-focus means for generating a magnetic selection-and-focus field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view and for changing the position in space of the field of view within an examination area, wherein said selection-and-focus means includes at least one set of selection-and-focus field coils and a selection-and-focus field generator unit for generating selection-and-focus field currents to be provided to said at least one set of selection-and-focus field coils for controlling the generation of said magnetic selection-and-focus field, wherein said at least one set of selection-and-focus field coils includes
at least one inner selection-and-focus field coil being formed as a closed loop about an inner coil axis, and
a group of at least two outer selection-and-focus field coils arranged at a larger distance from said inner coil axis than said at least one inner selection-and-focus field coil and at different angular positions, each outer selection-and-focus field coils being formed as a closed loop about an associated outer coil axis;

drive means including a drive field signal generator unit and drive field coils for changing the position in space and/or size of the two sub-zones in the field of view by means of a magnetic drive field so that the magnetization of the magnetic material changes locally; and wherein said at least one set of selection-and-focus field coils further includes
at least one pole shoe having a number of pole shoe segments carrying the various selection-and-focus field coils, and
a pole shoe yoke connecting said pole shoe segments.

7. An apparatus as claimed in claim 6, wherein said at least one pole shoe includes
at least one inner pole shoe segment carrying said at least one inner selection-and-focus field coil, and
at least two outer pole shoe segments arranged at a larger distance from said inner coil axis and each outer pole shoe segment carrying one of said at least two outer selection-and-focus field coils.

8. An apparatus as claimed in claim 6, wherein said at least one pole shoe includes at least four outer pole shoe segments each carrying an outer selection-and-focus field coil.

9. An apparatus as claimed in claim 6, wherein said at least one pole shoe includes four outer pole shoe segments each carrying an outer selection-and-focus field coil, said outer pole shoe segments being arranged at the same distance from the inner coil axis but angularly displaced by 90° with respect to each other.

10. An apparatus as claimed in claim 6, wherein said at least one pole shoe includes a second inner pole shoe segment (312) in the form of a closed ring around said first inner pole shoe segment (311), said second inner pole shoe segment (312) carrying said second inner selection-and-focus field coil.

11. An apparatus as claimed in claim 6, wherein at least the at least one inner pole shoe segment and head portions (313h, 314h) of the outer pole shoe segments (313, 314) facing the examination area are made from a soft-magnetic material having a high saturation induction.

12. An apparatus as claimed in claim 6, wherein the tail portions (313t, 314t) of the outer pole shoe segments (311, 314) facing away from the examination area and the pole shoe yoke are made from a soft-magnetic material having a lower saturation induction than the material of the inner pole shoe segments,.

13. An apparatus as claimed in claim 6,
wherein the pole shoes are made from magnetically conductive sheets, and
wherein sheets forming the inner pole shoe segments and an adjacent head portion (317h) of the pole shoe yoke are arranged in a direction parallel to the inner coil axis.

14. An apparatus as claimed in claim 6, wherein a cross section perpendicular to said inner coil axis through ahead portion (313h, 314h) of said outer pole shoe segments (313, 314) facing said examination area covers a larger area than a parallel cross section through a tail portion (313*t*, 314*t*) of said outer pole shoe segments (313, 314) facing away from said examination area.

15. An apparatus as claimed in claim 6, wherein at least two pole shoes are arranged on different sides of said examination area.

\* \* \* \* \*